(12) United States Patent
Luhmann

(10) Patent No.: US 12,405,276 B2
(45) Date of Patent: Sep. 2, 2025

(54) METHODS OF DETECTING SEPTIC ARTHRITIS, TRANSIENT SYNOVITIS AND OSTEOMYELITIS

(71) Applicant: Washington University, St. Louis, MO (US)

(72) Inventor: Scott Luhmann, St. Louis, MO (US)

(73) Assignee: Washington University, St. Louis, MO (US)

( * ) Notice: Subject to any disclaimer, the term of this patent is extended or adjusted under 35 U.S.C. 154(b) by 943 days.

(21) Appl. No.: 17/432,700

(22) PCT Filed: Feb. 21, 2020

(86) PCT No.: PCT/US2020/019352
§ 371 (c)(1),
(2) Date: Aug. 20, 2021

(87) PCT Pub. No.: WO2020/172622
PCT Pub. Date: Aug. 27, 2020

(65) Prior Publication Data
US 2022/0187314 A1 Jun. 16, 2022

Related U.S. Application Data

(60) Provisional application No. 62/808,598, filed on Feb. 21, 2019.

(51) Int. Cl.
*G01N 33/74* (2006.01)
*G01N 33/68* (2006.01)

(52) U.S. Cl.
CPC ..... *G01N 33/6893* (2013.01); *G01N 33/6869* (2013.01); *G01N 33/6887* (2013.01);
(Continued)

(58) Field of Classification Search
CPC .......... G01N 33/6893; G01N 33/6869; G01N 33/6887; G01N 33/74; G01N 2333/495;
(Continued)

(56) References Cited

U.S. PATENT DOCUMENTS

2016/0280791 A1 9/2016 Ghayur et al.
2017/0058027 A1 3/2017 Wu et al.

OTHER PUBLICATIONS

Hong et al. Measurement of interleukin-33 (IL-33) and IL-33 receptors (sST2 and ST2L) in patients with rheumatoid arthritis. J Korean Med Sci. Sep. 2011;26(9):1132-9. (Year: 2011).*
(Continued)

*Primary Examiner* — Christopher L Chin
*Assistant Examiner* — Ellis Follett Lusi
(74) *Attorney, Agent, or Firm* — Polsinelli PC

(57) ABSTRACT

The present disclosure provides methods for detecting septic arthritis, transient synovitis, or osteomyelitis, based on protein signatures. Specifically, the method comprising: (i) measuring expression levels of one or more proteins in a biological sample obtained from the subject; (ii) determining a protein signature correlated with a detected disease based on the expression levels of the proteins in step (i); and (iii) assessing the occurrence or severity of the subject correlated with the disease based on the protein signature determined in step (ii). The methods may further comprise identifying suitable treatment for the patient based on the protein signatures.

7 Claims, 11 Drawing Sheets

(52) U.S. Cl.
CPC ....... *G01N 33/74* (2013.01); *G01N 2333/495* (2013.01); *G01N 2333/5418* (2013.01); *G01N 2333/5753* (2013.01); *G01N 2333/78* (2013.01); *G01N 2800/102* (2013.01)

(58) Field of Classification Search
CPC ... G01N 2333/5418; G01N 2333/5753; G01N 2333/78; G01N 2800/102; C12Q 1/6883; C12Q 2600/158
USPC .............................. 436/501; 435/4, 7.1, 7.9
See application file for complete search history.

(56) References Cited

OTHER PUBLICATIONS

Horowitz et al. Approach to septic arthritis. Am Fam Physician. Sep. 15, 2011;84(6):653-60. (Year: 2011).*

Moskal et al. Serum levels of transforming growth factor alpha in gastrointestinal cancer patients. Cancer Epidemiol Biomarkers Prev. Mar. 1995;4(2):127-31 (Year: 1995).*

Lambeck et al. Serum cytokine profiling as a diagnostic and prognostic tool in ovarian cancer: a potential role for interleukin 7. Clin Cancer Res. Apr. 15, 2007;13(8):2385-91. (Year: 2007).*

Calcedo et al. Immune Responses in 101HEMB01, a Phase 1/2 Open-Label, Single Ascending Dose-Finding Trial of DTX101 (AAVrh10FIX) in Patients with Severe Hemophilia B. Blood 2017; 130 (Supplement 1): 3333. (Year: 2017).*

Imagama et al. Early diagnosis of septic arthritis using synovial fluid presepsin: A preliminary study. J Infect Chemother. Mar. 2019;25(3):170-174. Epub Nov. 23, 2018. (Year: 2018).*

International Preliminary Report on Patentability for International Application No. PCT/US2020/019352, mailed Sep. 2, 2021, 12 Pages.

International Search Report and Written Opinion for International Application No. PCT/US2020/019352, mailed Jul. 28, 2020, 17 Pages.

Ovrevik J., et al., "TACE/TGF-α/EGFR Regulates CXCL8 in Bronchial Epithelial Cells Exposed to Particulate Matter Components," European Respiratory Journal, 2011, vol. 38, No. 5, pp. 1189-1199.

Shirtliff M.E., et al., "Acute Septic Arthritis," Clinical Microbiology Reviews, 2002, vol. 15, No. 4, pp. 527-544.

Staurengo-Ferrari L., et al., "Interleukin-33 Receptor (ST2) Deficiency Improves the Outcome of *Staphylococcus aureus*-Induced Septic Arthritis," Frontiers in Immunology, May 2018, vol. 9, No. 962, pp. 1-14.

* cited by examiner

| ID | Diagnosis | WBC | ESR (mm/H) | CRP (mg/L) | C1-C2 | COMP | CS-846 | Hyaluronon | Procalcitonin | PIIANP | CTx-II | EGF (12) | FGF-2 (13) | Eotaxin-1 (14) | TGF-a (15) |
|---|---|---|---|---|---|---|---|---|---|---|---|---|---|---|---|
| 1 | Septic Arthritis | 10.3 | 86.0 | 7.8 | 0.405 | 405.6 | 316.585 | 22.426 | 2.925 | 6209.655 | 93.25 | 121.47 | 102.79 | 30.68 | 6.33 |
| 2 | Septic Arthritis | 8.5 | 75.0 | 15.6 | 0.388 | 137.65 | 570.4975 | 42.476 | 2.925 | 3782.055 | 81.08 | 113.64 | 73.92 | 60.04 | 4.4 |
| 3 | Septic Arthritis | 6.9 | 45.0 | 5.9 | 0.479 | 75.25 | 256.055 | 17.512 | 219.597 | 1488.474 | 80.89 | 147.41 | 111.55 | 93.77 | 8.45 |
| 4 | Septic Arthritis | 10.1 | 22.0 | 228 | 0.063 | 122.55 | 287.028 | 118.974 | 3434.288 | 575.5125 | 131.4075 | 67.81 | 71.89 | 111.2 | 12.42 |
| 5 | Septic Arthritis | 13.8 | 60.0 | 24 | 0.495 | 89.725 | 167.7575 | 7.706 | 85.098 | 3842.47 | 96.1 | 45.28 | 35.08 | 50.21 | 4.94 |
| 6 | Septic Arthritis | 10.6 | 31.0 | 14.2 | 0.368 | 374.95 | 360.77 | 55.958 | 84.369 | 3373.847 | 85.055 | 116.17 | 90 | 96.9 | 8.23 |
| 7 | Septic Arthritis | 12.4 | 92.0 | 221.7 | 0.132 | 150.1 | 314.455 | 37.148 | 2272.631 | 1021.505 | 93.54 | 102.5 | 168.18 | 115.69 | 33.35 |
| 8 | Septic Arthritis | 8.63 | 12.0 | 29.8 | 0.302 | 103.625 | 207.1675 | 6.622 | 285.684 | 1996.48 | 73.435 | 293.16 | 298.15 | 57.72 | 17.9 |
| 9 | Septic Arthritis | 12.06 | 34.0 | 3.2 | 0.469 | 111.25 | 363.0025 | 14.222 | 91.329 | 2145.063 | 95.41 | 299.22 | 94.72 | 106.17 | 3.16 |
| 10 | Septic Arthritis | 8.4 | 23.0 | 36.6 | 0.483 | 48.325 | 175.18 | 8.172 | 4.3875 | 1994.189 | 82.82 | 178.52 | 15.72 | 52.51 | 13.54 |
| 11 | Septic Arthritis | 12.2 | 73.0 | 28 | 0.49 | 156.35 | 196.9075 | 7.94 | 163.485 | 3886.106 | 88.925 | 83.26 | 91.6 | 82.9 | 12.14 |
| 12 | Toxic Synovitis | 15.8 | 10.0 | 43.7 | 0.455 | 300.675 | 414.245 | 16.092 | 61.044 | 1786.283 | 77.57 | 40.02 | 126.1 | 48.65 | 12.78 |
| 13 | Toxic Synovitis | 7.6 | 7.0 | 0.4 | 0.628 | 179.55 | 244.6475 | 11.164 | 50.507 | 1651.568 | 77.285 | 43.1 | 30.19 | 49.61 | 1.33 |
| 14 | Toxic Synovitis | 15.5 | 7.0 | 0.5 | 0.146 | 353.625 | 351.305 | 22.826 | 140.82 | 461.568 | 74.9 | 683.72 | 77.8 | 122.6 | 4.59 |
| 15 | Toxic Synovitis | 11.2 | 6.0 | 0.2 | 0.299 | 0 | 165.2125 | 19.542 | 145.528 | 126.258 | 12.85 | 10000 | 10.23 | 4.28 | 2.37 |
| 16 | Toxic Synovitis | 11.8 | 19.0 | 31.7 | 0.153 | 189.5 | 271.1825 | 10.324 | 69.8 | 840.403 | 60.715 | 85.93 | 86.7 | 155.13 | 3 |
| 17 | Toxic Synovitis | 7.3 | 4.0 | 0.6 | 0.571 | 326.125 | 431.8675 | 12.984 | 53.337 | 4476.119 | 101.6 | 167.6 | 130.58 | 34.46 | 4.99 |
| 18 | Toxic Synovitis | 17.6 | 50.0 | 67.1 | 0.268 | 133.575 | 282.5225 | 14.038 | 198.234 | 2336.192 | 77.135 | 120.45 | 158.46 | 61.79 | 17.38 |
| 19 | Toxic Synovitis | 8.7 | 8.0 | 0.5 | 0.548 | 258.275 | 215.26 | 16.618 | 2.925 | 2601.003 | 65.325 | 67.1 | 63.09 | 95.3 | 2.55 |
| 20 | Toxic Synovitis | 5.4 | 11.0 | 0.8 | 0.676 | 279.9 | 241.73 | 11.2 | 77.36 | 7291.929 | 95.655 | 18.61 | 27.37 | 65.22 | 0.41 |
| 21 | Toxic Synovitis | 10.1 | 7.0 | 1.2 | 0.398 | 139 | 219.2775 | 18.058 | 165.932 | 1469.203 | 68.555 | 113.91 | 65.41 | 47.92 | 1.25 |
| 22 | Toxic Synovitis | 10.5 | 10.0 | 3.6 | 0.474 | 531.65 | 287.2675 | 20.59 | 2.925 | 2031.08 | 71.225 | 109.13 | 91.6 | 69.86 | 2.76 |

FIG. 5

| ID | Diagnosis | G-CSF (18) | Flt-3L (19) | GM-CSF (20) | Fractalkine (21) | IFNa2 (22) | IFNy (25) | GRO alpha (26) | IL-10 (27) | MCP-3 (28) | IL-12P40 (29) | MDC (30) | IL-12P70 (33) | PDGF-AA (34) | IL-13 (35) | PDGF-BB (36) |
|---|---|---|---|---|---|---|---|---|---|---|---|---|---|---|---|---|
| 1 | Septic Arthritis | 58.73 | 0.44 | 29.44 | 32.07 | 1.6 | 3.1 | 3501.51 | 12.81 | 31.48 | 66.4 | 1454.97 | 0.4 | 456.22 | 0.145 | 6840.81 |
| 2 | Septic Arthritis | 45.89 | 0.44 | 24.65 | 60.55 | 48.43 | 31.9 | 12558.9 | 8.61 | 22.95 | 66.4 | 2474.04 | 5.85 | 1997.67 | 3.79 | 5626.82 |
| 3 | Septic Arthritis | 8.99 | 10.44 | 112.67 | 19.58 | 47.12 | 37.59 | 1421.38 | 3 | 69.9 | 307.27 | 763.99 | 7.26 | 1188.16 | 23.42 | 3633.25 |
| 4 | Septic Arthritis | 2317.45 | 13.03 | 43.12 | 242.06 | 17.71 | 871.37 | 1737.12 | 430.77 | 50.07 | 135.87 | 364.76 | 79.2 | 910.74 | 0.145 | 9805.68 |
| 5 | Septic Arthritis | 2 | 0.44 | 19.3 | 17.76 | 6.95 | 4.27 | 1777.02 | 0.1 | 1.69 | 4.48 | 655.28 | 0.16 | 3569.16 | 0.145 | 4898.84 |
| 6 | Septic Arthritis | 31.22 | 0.44 | 7.71 | 356.47 | 30.39 | 30.25 | 1265.87 | 3.08 | 35.82 | 54.81 | 567.19 | 2.82 | 5408.48 | 3.79 | 9805.68 |
| 7 | Septic Arthritis | 1061.13 | 0.44 | 48.34 | 168.92 | 49.73 | 57.76 | 1708.68 | 92.14 | 30.57 | 47.96 | 2575.8 | 84.53 | 3491.37 | 0.85 | 9805.68 |
| 8 | Septic Arthritis | 4.26 | 72.12 | 60.63 | 21.47 | 33.33 | 81.56 | 1625.15 | 13.14 | 40.18 | 58.89 | 1255.28 | 118.76 | 1944.18 | 45.68 | 4094.17 |
| 9 | Septic Arthritis | 22.8 | 23.17 | 31.25 | 21.47 | 44.47 | 50.39 | 2057.18 | 2.32 | 23.97 | 87.9 | 2228.17 | 13.57 | 2944.04 | 0.145 | 5008.03 |
| 10 | Septic Arthritis | 3.53 | 0.44 | 14.4 | 9.42 | 17.71 | 3.5 | 27189.92 | 3.82 | 0.11 | 4.48 | 468.97 | 0.16 | 3275.14 | 0.29 | 4708.73 |
| 11 | Septic Arthritis | 10.19 | 0.87 | 104.65 | 12.64 | 10.65 | 11.95 | 2035.38 | 2.71 | 25.52 | 95.49 | 582.43 | 2.08 | 3064.96 | 0.145 | 9805.68 |
| 12 | Toxic Synovitis | 103.72 | 1.57 | 45.76 | 32.07 | 54.85 | 82.99 | 3153.61 | 14.02 | 22.73 | 43.94 | 1211.15 | 6.62 | 729.45 | 0.145 | 9805.68 |
| 13 | Toxic Synovitis | 4.26 | 0.44 | 6.87 | 6.29 | 21.04 | 2.24 | 27189.92 | 0.91 | 0.11 | 1.54 | 645.65 | 0.025 | 2111.46 | 0.145 | 9805.68 |
| 14 | Toxic Synovitis | 25.77 | 0.44 | 27.58 | 47.97 | 41.77 | 12.08 | 1700.2 | 4.16 | 24.37 | 62.72 | 1264.53 | 4.97 | 3334.09 | 0.145 | 6156.8 |
| 15 | Toxic Synovitis | 18.9 | 0.44 | 0.32 | 54.11 | 1.6 | 0.32 | 3.78 | 0.05 | 0.11 | 77.89619 | 9.34 | 0.05 | 407.1 | 0.145 | 9.165 |
| 16 | Toxic Synovitis | 14.63 | 0.44 | 201.45 | 239.37 | 36.2 | 9.07 | 578.15 | 2.36 | 44.71 | 75.22 | 1028.19 | 9.51 | 2303.59 | 6.83 | 9805.68 |
| 17 | Toxic Synovitis | 26.65 | 11.14 | 48.7 | 45.05 | 49.73 | 2.68 | 3080.65 | 2.04 | 33.51 | 95.49 | 773.78 | 0.64 | 2464.9 | 0.145 | 4257.87 |
| 18 | Toxic Synovitis | 274.97 | 0.44 | 45.76 | 114.15 | 44.47 | 144.43 | 2990.93 | 51.12 | 43.61 | 114.32 | 1478.92 | 116.27 | 1199.74 | 25.95 | 5347.89 |
| 19 | Toxic Synovitis | 30.52 | 2.27 | 29.9 | 6.29 | 31.87 | 4.27 | 1162.22 | 4.33 | 11.07 | 45.35 | 1313.99 | 0.64 | 1793.35 | 0.145 | 9805.68 |
| 20 | Toxic Synovitis | 3.53 | 0.44 | 38.82 | 16 | 19.4 | 2.46 | 1062.21 | 12.27 | 0.11 | 42.46 | 1475.79 | 0.025 | 1811.64 | 0.145 | 3714.14 |
| 21 | Toxic Synovitis | 3.53 | 2.27 | 36.38 | 25.47 | 21.04 | 5 | 1848.53 | 1.03 | 13.8 | 83.06 | 1775.24 | 0.025 | 2520.41 | 0.145 | 3846.83 |
| 22 | Toxic Synovitis | 38.47 | 0.44 | 53.71 | 96.96 | 43.12 | 19.62 | 586.56 | 3.82 | 59.16 | 141.77 | 1468.5 | 11 | 1369.09 | 7.79 | 9805.68 |

| ID | Diagnosis | IL-15 (37) MCP_1_67 | sCD40L (38) MIP_1a_72 | IL-17A (39) MIP_1B_73 | IL-1RA (42) RANTES_74 | IL-1a (44) TNFa_75 | IL-9 (45) TNFB_76 | IL-1B (46) VEGF_A_78 | IL-2 (48) IL_18_66 | IL-3 (51) Eotaxin_12 | IL-4 (53) MCP_2_13 | IL-5 (55) BCA_1_15 | IL-6 (57) MCP_4_18 | IL-7 (61) I_309_19 | IL-8 (63) IL_16_21 | IP-10 (65) TARC_26 |
|---|---|---|---|---|---|---|---|---|---|---|---|---|---|---|---|---|
| 1 | Septic Arthritis | 265.58 | 22.34 | 64.33 | 540.47 | 12.38 | 0 | 7.9 | 30.4 | 273.13 | 27.36 | 38.58 | 1.43 | 1.42 | 1.22 | 122.58 |
| 2 | Septic Arthritis | 489.18 | 26.27 | 74.03 | 358.27 | 37.08 | 8.41 | 322.85 | 95.76 | 746.98 | 17.66 | 123.96 | 52.26 | 5.49 | 183.13 | 75.01 |
| 3 | Septic Arthritis | 256.57 | 9.24 | 174.44 | 568.02 | 9.96 | 5.367143 | 149.31 | 136.15 | 911.31 | 22.75 | 71.71 | 0.715 | 0.66 | 1.22 | 78.85 |
| 4 | Septic Arthritis | 1048.51 | 39.22 | 253.5 | 1366.25 | 257.8 | 1.07 | 83.71 | 287.82 | 236.6 | 457.02 | 148.24 | 93.31 | 6.75 | 287.9 | 110.91 |
| 5 | Septic Arthritis | 215.91 | 5.57 | 34.25 | 3.6 | 9.76 | 0 | 75.3 | 138.35 | 1001.02 | 18.83 | 91.39 | 3.45 | 1.39 | 1.22 | 34.85 |
| 6 | Septic Arthritis | 206.56 | 7.82 | 57.56 | 295.73 | 14.5 | 15.01 | 380.55 | 79.15 | 3839.49 | 65.88 | 70.95 | 78.71 | 2.6 | 188.76 | 124.45 |
| 7 | Septic Arthritis | 756.25 | 20.44 | 128.86 | 609.54 | 20.69 | 5.14 | 487.05 | 213.48 | 1574.02 | 38.41 | 71.88 | 21.92 | 3.47 | 1.22 | 703.13 |
| 8 | Septic Arthritis | 224.46 | 17.67 | 148.73 | 2156.35 | 31.75 | 0 | 162.39 | 180 | 885.95 | 30.83 | 54.58 | 2.44 | 1.3 | 1.22 | 15.74 |
| 9 | Septic Arthritis | 297.6 | 10.63 | 63.93 | 311.72 | 24.35 | 0 | 257.27 | 171.17 | 2221.59 | 36.35 | 112.3 | 73.96 | 2.05 | 227.4 | 243.62 |
| 10 | Septic Arthritis | 139.97 | 37.89 | 45.81 | 848.83 | 13.39 | 0 | 60.17 | 46.09 | 2136.62 | 27.36 | 28.88 | 11.52 | 1.58 | 1.22 | 91.12 |
| 11 | Septic Arthritis | 244.34 | 6.23 | 80.61 | 435.33 | 10.87 | 1.92 | 67.3 | 93.32 | 949.78 | 27.19 | 33.92 | 23.52 | 1.3 | 84.62 | 36.67 |
| 12 | Toxic Synovitis | 437.48 | 18.07 | 100.49 | 290.36 | 22.93 | 4.06 | 287.58 | 96.57 | 303.63 | 89.25 | 153.77 | 4.97 | 0.66 | 568.07 | 88.71 |
| 13 | Toxic Synovitis | 300.69 | 4.65 | 34.25 | 452.92 | 18.61 | 8.41 | 14.01 | 32.67 | 279.02 | 43.8 | 20.87 | 0.715 | 1.27 | 1.22 | 89.87 |
| 14 | Toxic Synovitis | 1786.67 | 17.12 | 91.35 | 1647.04 | 46.67 | 0 | 57.05 | 142.34 | 2305.79 | 53.76 | 50.39 | 47.36 | 2.21 | 18.08 | 224.57 |
| 15 | Toxic Synovitis | 351.81 | 2.06 | 2.58 | 3.6 | 0.4 | 0 | 125.29 | 13.82 | 1307.39 | 1.945 | 0.12 | 0.715 | 0.235 | 1.22 | 0.11 |
| 16 | Toxic Synovitis | 654.58 | 15 | 99.36 | 812.85 | 22.88 | 11.48 | 34.12 | 181.34 | 3687.7 | 44.45 | 29.97 | 103.64 | 2.64 | 1149.13 | 37.02 |
| 17 | Toxic Synovitis | 83.54 | 20.08 | 107.9 | 284.09 | 27.21 | 2.13 | 119.91 | 12.07 | 899.02 | 26.48 | 111.63 | 7.05 | 2.77 | 477.75 | 87.48 |
| 18 | Toxic Synovitis | 699.25 | 29.07 | 167.79 | 149.4 | 42.51 | 21.15 | 138.38 | 102.19 | 1073.95 | 110.68 | 100.66 | 215.69 | 7.93 | 351.72 | 135.18 |
| 19 | Toxic Synovitis | 273.67 | 4.46 | 55.74 | 829.6 | 16.63 | 0 | 140.4748 | 231.85 | 559.91 | 39.71 | 38.39 | 61.07 | 3.09 | 35.91 | 268.29 |
| 20 | Toxic Synovitis | 350.53 | 14.44 | 37.2 | 175.47 | 10.36 | 0 | 6.04 | 176.62 | 251.98 | 84.95 | 51.39 | 0.715 | 1.91 | 1.22 | 45.17 |
| 21 | Toxic Synovitis | 300.38 | 14.5 | 74.03 | 756.65 | 17.85 | 0 | 11.48 | 65.51 | 920.48 | 24.01 | 15.79 | 3.96 | 1.78 | 1.22 | 102.38 |
| 22 | Toxic Synovitis | 433.92 | 13.63 | 101.77 | 535.31 | 21.91 | 33.93 | 102.31 | 76.59 | 2397.23 | 48.72 | 47.46 | 126.95 | 7.82 | 433.98 | 93.13 |

| ID | Diagnosis | MCP-1 (67) | MIP-1a (72) | MIP-1B (73) | RANTES (74) | TNFa (75) | TNFB (76) | VEGF-A (78) | IL-18 (66) | Eotaxin (12) | MCP-2 (13) | BCA-1 (15) | MCP-4 (18) | I-309 (19) | IL-16 (21) | TARC (26) | 6CKine (28) |
|---|---|---|---|---|---|---|---|---|---|---|---|---|---|---|---|---|---|
| ID | Diagnosis | 6CKine_28 | Eotaxin_3_30 | LIF_34 | TPO_36 | SCF_38 | TSLP_43 | IL_33_45 | IL_20_51 | IL_21_52 | IL_23_54 | TRAIL_56 | CTACK_62 | SDF_1a_B_64 | ENA_78_66 | MIP_1d_76 | IL_28A_77 |
| 1 | Septic Arthritis | 282.12 | 5.45 | 0.01 | 142.98 | 3.02 | 1.22 | 2.44 | 1.81 | 0.09 | 24.415 | 10.13 | 413.78 | 2050.181 | 3024.28 | 1743.13 | 1.22 |
| 2 | Septic Arthritis | 1171.74 | 5.54 | 34.73 | 2046.68 | 116.45 | 124.64 | 202.25 | 1.81 | 5.98 | 9816.15 | 121.28 | 794.64 | 1655.42 | 1833.61 | 4583.14 | 98.2 |
| 3 | Septic Arthritis | 56.17 | 3.11 | 0.01 | 3600.17 | 3.02 | 61.59 | 224.83 | 1.81 | 1.84 | 6674.16 | 1.22 | 410.95 | 802.42 | 502.04 | 1579.55 | 1.22 |
| 4 | Septic Arthritis | 353.26 | 8.49 | 15.05 | 820.89 | 39.29 | 12.79 | 44.93 | 119.55 | 3.22 | 746.3 | 71.35 | 1682.14 | 2610.89 | 238.32 | 2335.16 | 264.2 |
| 5 | Septic Arthritis | 75.6 | 4.09 | 0.01 | 18.25 | 3.02 | 1.22 | 2.44 | 1.81 | 0.09 | 24.415 | 16.98 | 670.14 | 965.8 | 1431.78 | 1292.04 | 1.22 |
| 6 | Septic Arthritis | 891.6 | 17.01 | 127.44 | 10515.13 | 133.59 | 509.32 | 761.92 | 305.43 | 10.97 | 39325.14 | 110.59 | 468.9 | 2167.12 | 879.84 | 2301.96 | 141.12 |
| 7 | Septic Arthritis | 366.32 | 3.7 | 0.01 | 598.27 | 3.02 | 1.22 | 2.44 | 1.81 | 0.09 | 24.415 | 5.65 | 1938.98 | 802.42 | 277.78 | 2896.03 | 1.22 |
| 8 | Septic Arthritis | 238.42 | 3.31 | 0.01 | 0.045 | 3.02 | 1.22 | 2.44 | 1.81 | 0.09 | 24.415 | 41.89 | 453.21 | 1324.5 | 1146.23 | 1246.08 | 1.22 |
| 9 | Septic Arthritis | 299.14 | 4.77 | 132.15 | 1125.64 | 6.04 | 147.17 | 128.69 | 1.81 | 1.71 | 7041.95 | 67.24 | 857.37 | 10250.09 | 1327.34 | 1797.05 | 232.3867 |
| 10 | Septic Arthritis | 102.16 | 8.3 | 0.01 | 1449.09 | 3.02 | 1.22 | 16.87 | 1.81 | 0.46 | 178.82 | 28.35 | 609.15 | 753.78 | 5738.57 | 2031.17 | 1.22 |
| 11 | Septic Arthritis | 330.06 | 6.59 | 3.66 | 1339.57 | 3.02 | 13.48 | 53.63 | 57.1 | 1.84 | 878.3 | 28.49 | 648.42 | 2121.14 | 469.89 | 1364.31 | 81.11 |
| 12 | Toxic Synovitis | 366.32 | 5.16 | 0.01 | 1483.43 | 3.02 | 21.66 | 66.21 | 9.34 | 5.16 | 1301.57 | 53.94 | 491.5 | 552.72 | 2004.72 | 1793.99 | 728.46 |
| 13 | Toxic Synovitis | 144.27 | 3.11 | 0.01 | 0.045 | 3.02 | 1.22 | 2.44 | 1.81 | 0.09 | 24.415 | 89.7 | 520.8 | 390.63 | 1772.42 | 968.68 | 1.22 |
| 14 | Toxic Synovitis | 113.61 | 3.99 | 0.01 | 0.045 | 3.02 | 1.22 | 2.44 | 1.81 | 0.09 | 24.415 | 65.82 | 751.16 | 881.82 | 1715.82 | 3413.98 | 1.22 |
| 15 | Toxic Synovitis | 9.765 | 1.71 | 0.01 | 98.96 | 3.02 | 11.05 | 19.66 | 1.81 | 8.61 | 24.415 | 5.51 | 8.18 | 2050.181 | 12.645 | 6.105 | 1.22 |
| 16 | Toxic Synovitis | 793.57 | 24.65 | 655.96 | 6656.85 | 289.54 | 360.48 | 482.83 | 339.65 | 22.97 | 27221.35 | 107 | 483.93 | 2970.64 | 414.65 | 1720.25 | 1841.19 |
| 17 | Toxic Synovitis | 390.91 | 5.25 | 0.01 | 514.91 | 3.02 | 1.22 | 34.17 | 61.6 | 8.19 | 391.46 | 41.89 | 836.33 | 1566.26 | 1497.42 | 2098.73 | 576.46 |
| 18 | Toxic Synovitis | 1078.36 | 28.27 | 320.13 | 3563.81 | 259.32 | 109.17 | 199.04 | 352.5 | 29.05 | 10989.22 | 94.25 | 1246.57 | 3858.52 | 585.85 | 1183.65 | 438.93 |
| 19 | Toxic Synovitis | 552.13 | 14.44 | 43.43 | 560.29 | 12.57 | 5.31 | 35.49 | 205.91 | 15.19 | 489.9 | 52 | 495.88 | 1536.08 | 660.49 | 1698.47 | 135.27 |
| 20 | Toxic Synovitis | 107.83 | 3.7 | 0.01 | 0.045 | 3.02 | 1.22 | 2.44 | 1.81 | 0.09 | 24.415 | 126.29 | 701.94 | 1467.23 | 608.74 | 5683.53 | 1.22 |
| 21 | Toxic Synovitis | 163.9 | 3.31 | 0.01 | 134.91 | 3.02 | 1.22 | 2.44 | 1.81 | 0.09 | 24.415 | 63.99 | 581.55 | 790.51 | 771.75 | 1642.29 | 1.22 |
| 22 | Toxic Synovitis | 1245.03 | 54.24 | 153.52 | 5192.37 | 236.67 | 172.64 | 325.33 | 360.95 | 28.42 | 14222.03 | 140.33 | 536.41 | 3535.62 | 426.8 | 1279.13 | 561.76 |

FIG. 5 Continued

METHODS OF DETECTING SEPTIC ARTHRITIS, TRANSIENT SYNOVITIS AND OSTEOMYELITIS

CROSS REFERENCE TO RELATED APPLICATIONS

This application claims the benefit of International Application No. PCT/US2020/019352, filed Feb. 21, 2020 which claims the benefit of U.S. Provisional Application 62/808, 598, filed Feb. 21, 2019, the disclosures of which are hereby incorporated by reference in their entirety.

FIELD OF THE TECHNOLOGY

This disclosure generally relates to methods of detecting, monitoring and/or treating septic arthritis or osteomyelitis caused by or as a result of bacterial infections. Another aspect of the present technology relates to method of methods of detecting, monitoring and/or treating transient synovitis caused by or as a result of viral infections. The present disclosure also relates to detection, prognosis, and/or treatment of bacterial infections of the bone, bone marrow, joint, and synovial fluid.

BACKGROUND

Musculoskeletal infections are a global problem. In the U.S. alone in 2012, there were 13,714 hospitalizations for septic arthritis, as the primary diagnosis in all age groups, with a population of 314 million (Singh Ja, et al., PLoS One 2017; 12: e0182577). Extrapolating to the worldwide population of >7.6 billion people in 2018 there would be >330,000 cases this year alone. In adults, 21% of those with septic arthritis have a poor outcome at 10 years after infection of the affected joint (Christiansen P, et al., J Pediatr Orthop B 1999; 8:302-5; Studahl M et al., Scand Infect Dis 1994; 26:85-93). In both the adult and pediatric populations, the adverse outcomes after septic arthritis are well known: destruction of articular cartilage, early-onset osteoarthritis, osteonecrosis, and long-term daily joint pain and permanent physical disability, which can negatively impact quality of life (Dobbs M B et al., J Pediatr Orthop 2003; 23:162-8). Pediatric mortality rates for septic arthritis are currently unknown; however, multiple studies have demonstrated increased mortality rates with septic arthritis in the adult population (Andreasen R A et al., Scan J Rheumatol 2017; 46:27-32; Mahakkanukrauh A et al., Int J Rheum Dis 2013; 16:387-91; Oh D H W, et al., Clin Orthop Relat Res 2018; 476:1557-1565; Wu et al., BMC Geriatr 2017; 17:176).

The presentation of the acutely painful joint/limb is a diagnostic dilemma due to the similarity of presentations of the most likely diagnoses (septic arthritis, transient synovitis, and osteomyelitis) when the patient presents early after the onset of symptoms. The work-up has typically relied upon patient history, serum laboratory tests, radiologic imaging, and arthrocentesis. Identifying causation can be elusive, requiring extensive radiologic evaluation (ultrasound, magnetic resonance imaging, and computed tomography), multiple serum laboratory tests and invasive, painful procedures requiring conscious/deep sedation or general anesthesia (arthrocentesis, biopsy, irrigation/debridement). Since early diagnosis and treatment typically portends a better outcome, especially for septic arthritis, there is a need to determine the etiology of the problem urgently and accurately. Ideal treatment is the rapid, accurate identification of the septic arthritis, operative irrigation and debridement of the joint space and synovium (open or arthroscopic) and appropriate intravenous antibiotics.

Over the last 20+ years, there have been minimal meaningful clinical advancements in the diagnostic process of acute-onset, non-traumatic joint/extremity pain in pediatric patients, especially in the area of serum testing. The most common diagnoses for this clinical presentation are septic arthritis, osteomyelitis and non-bacterial etiologies, specifically viral-mediated transient synovitis. This has forced clinicians to continue to rely upon non-specific serum tests, such as erythrocyte sedimentation rate (ESR), C-reactive protein (CRP), and white blood cell counts (WBC). Due to the lack of innovation in this area, most research efforts over the last 15+ years have focused on developing predictive algorithms utilizing these non-specific assays. However, these algorithms have produced conflicting results and have not been able to demonstrate a positive impact clinical care.

The cost of the diagnostic work-up, at presentation, is dependent on multiple factors from the history of symptom onset, the clinical course and patient comorbidities. A basic Emergency Department work-up, consisting of physician consultations, facility charges, laboratory fees, arthrocentesis and radiologic imaging can exceed $3000 for uncomplicated cases of viral-mediated transient synovitis. As the complexity of the case increases, charges can escalate rapidly with advanced imaging (e.g. magnetic resonance imaging), surgical treatment (irrigation and debridement surgery) and inpatient care. In 2000, the national U.S. median length of hospital stay for septic arthritis was 5 days with median inflation-adjusted total charges of $11,155 per patient (Freedman J et al., J Pediatr Orthop 2006; 26:709-15). In 2012, there were 13,714 hospitalizations (all ages) with diagnosis of septic arthritis, with a mean inpatient stay of 7.2 days and annual U.S. total charges of $759 million (Singh Ja, et al., PLoS One 2017; 12: e0182577).

Thus a need in the art exists for a clinically applicable methods capable of being performed in the laboratory of hospitals, or as rapid screen point-of-care test for accurate detection of musculoskeletal infections (e.g., septic arthritis and osteomyelitis) and non-bacterial etiologies such as viral-mediated transient synovitis and used to guide treatment decisions.

SUMMARY

The present disclosure is based on the unexpected discovery of biomarker signatures, e.g., a septic arthritis protein signature, a transient synovitis protein signature and an osteomyelitis protein signature as disclosed herein, which correlate with disease occurrence, severity, and/or patient responsiveness to treatment. Such protein signatures can help determine suitable treatment for subjects in need thereof, for example, pediatric subjects with septic arthritis.

Accordingly, one aspect of the present disclosure provides a method for identifying a subject having septic arthritis by (i) measuring expression levels of one or more of TGFα, IL-7, IL-33 and IL-28A in a biological sample obtained from the subject; (ii) determining a septic arthritis protein signature based on the expression levels of the proteins in step (i); and (iii) assessing septic arthritis occurrence or severity of the subject based on the protein signature determined in step (ii). In some embodiments, the biological sample is a blood sample. In one aspect, the blood sample is a serum sample.

In some embodiments, the expression levels of the proteins are measured by an epitope binding agent assay, enzymatic assay, electrophoresis, chromatography, mass spectrometry, RT-PCR or microarray analysis. In some embodiments, the subject is identified as having or at risk for septic arthritis and the method further comprises subjecting the subject to a treatment of septic arthritis. In some aspects, the subject has undergone a prior treatment of septic arthritis.

In some embodiments, increased expression levels of the protein measured in step (i) relative to a reference value indicates the subject has septic arthritis. In another embodiment, increased TGFα or IL-7 relative to a reference value of a subject having transient synovitis indicates the subject has septic arthritis.

In another aspect, the present disclosure provides a method of identifying a subject having transient synovitis by (i) measuring expression levels of one or more of TGFα, IL-7, IL-33 and IL-28A in a biological sample obtained from the subject; (ii) determining a transient synovitis protein signature based on the expression levels of the proteins in step (i); and (iii) assessing transient synovitis occurrence or severity of the subject based on the protein signature determined in step (ii). In some embodiments, the biological sample is a blood sample. In one aspect, the blood sample is a serum sample.

In some embodiments, the expression levels of the proteins are measured by an epitope binding agent assay, enzymatic assay, electrophoresis, chromatography, mass spectrometry, RT-PCR or microarray analysis. In some embodiments, the subject is identified as having or at risk for transient synovitis and the method further comprises subjecting the subject to a treatment of viral synovitis. In some embodiments, increased expression levels of the protein measured in step (i) relative to a reference value indicates the subject has transient synovitis. In another embodiments, increased expression of TGFα or IL-7 relative to a reference value from a healthy control and decreased relative to a reference value from a subject having septic arthritis indicates the subject has transient synovitis.

In still another aspect, the present disclosure provides a method of identifying a subject having osteomyelitis by (i) measuring expression levels of one or more of procalcitonin, Type II collagen degradation (CTX-II), Type IIA Collagen N-Propeptide (PIIANP), and C1-2C Bone and Cartilage Degradation (C1-2C) in a biological sample obtained from the subject; (ii) determining a osteomyelitis protein signature based on the expression levels of the proteins in step (i); and (iii) assessing osteomyelitis occurrence or severity of the subject based on the protein signature determined in step (ii). In some embodiments, the biological sample is a blood sample. In one aspect, the blood sample is a serum sample, In some embodiments, the expression levels of the proteins are measured by an epitope binding agent assay, enzymatic assay, electrophoresis, chromatography, mass spectrometry, RT-PCR or microarray analysis. In some embodiments, the subject is identified as having or at risk for osteomyelitis and the method further comprises subjecting the subject to a treatment of osteomyelitis. In one aspect, the subject has undergone a prior treatment of osteomyelitis. In some embodiments, increased expression levels of the protein measured in step (i) relative to a reference value indicates the subject has osteomyelitis.

BRIEF DESCRIPTION OF THE FIGURES

FIG. 2A shows the serum concentration of C1-2C bone and cartilage degradation product (C1-C2).

FIG. 2B shows the serum concentration of type IIA collage n-propeptide (PIIANP).

FIG. 2C shows the serum concentration of cartilage oligometric matrix protein (COMP).

FIG. 2D shows the serum concentration of CS-846 aggrecan cartilage synthesis (CS-846).

FIG. 2E shows the serum concentration of cartilage oligometric matrix protein (COMP).

FIG. 2F shows the serum concentration of C-terminal telopeptide of type II collagen (CTX-II).

FIG. 4A shows the serum concentration of Transforming growth factor alpha (TGF-α). FIG. 4B shows the serum concentration of interleukin 7 (IL-7). FIG. 4C shows the serum concentration of interleukin 33 (IL-33). FIG. 4D shows the serum concentration of interleukin 28 (IL-28A).

FIG. 5 shows a table of the 65 unique cytokines and chemokines in the serum of patients with viral synovitis, septic arthritis, and healthy controls.

DETAILED DESCRIPTION

Figure 1:
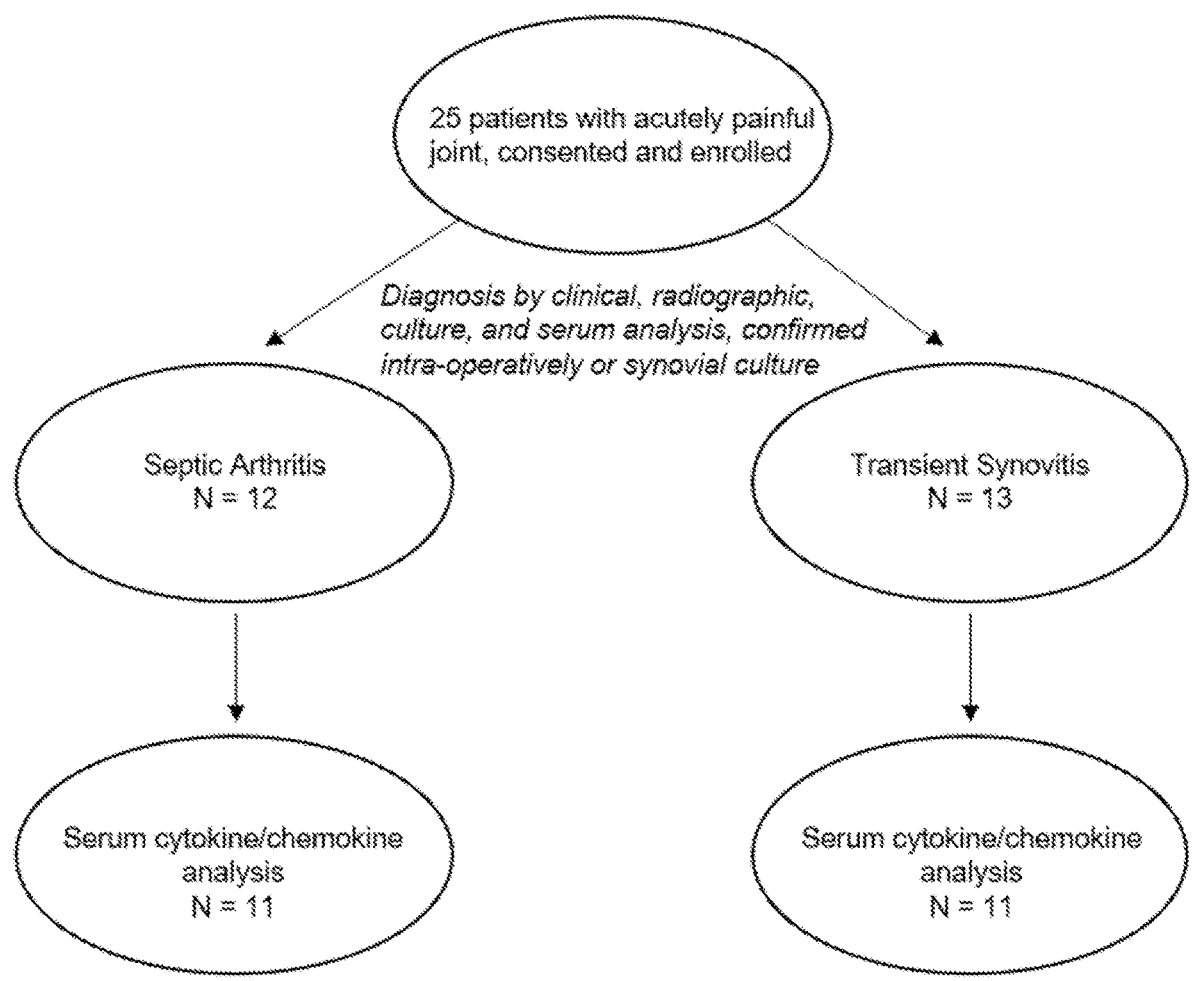
FIG. 1 shows a flowchart of patient enrolment, diagnosis, and analysis.
Figure 2A:
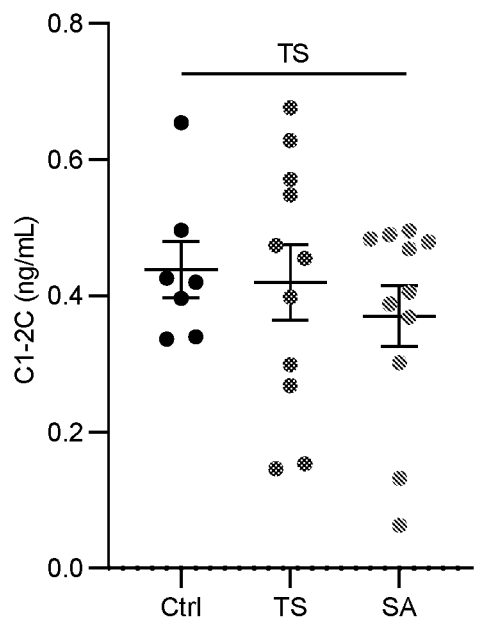
FIG. 2A-2F are graphs showing the serum concentration of C1-2C bone and cartilage degradation product (C1-C2), cartilage oligometric matrix protein (COMP), CS-846 aggrecan cartilage synthesis (CS-846), hyaluronan, type IIA collage n-propeptide (PIIANP), and C-terminal telopeptide of type II collagen (CTX-II).
Figure 2B:
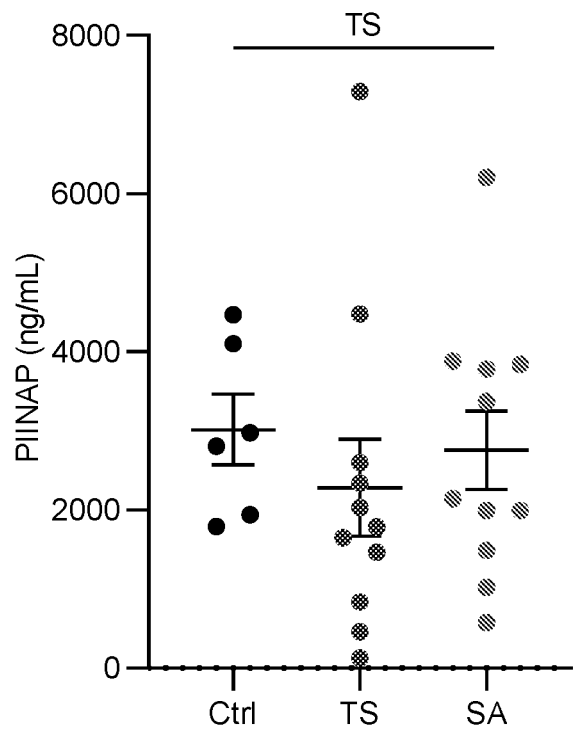
Figure 2C:
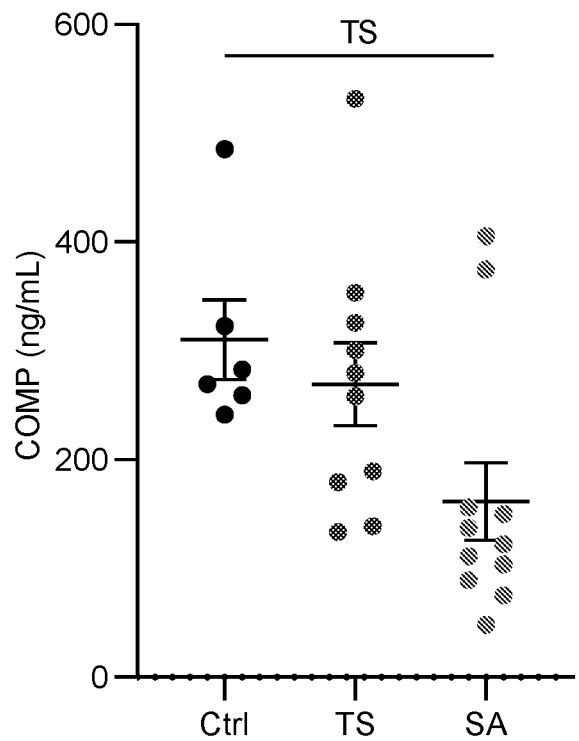
Figure 2D:
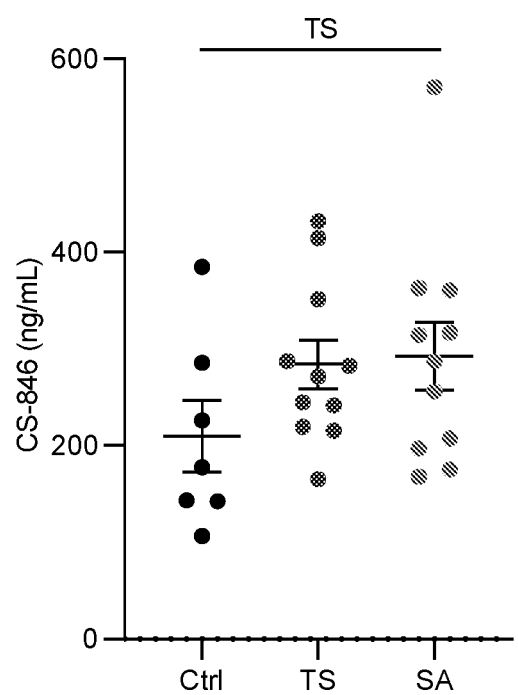
Figure 2E:
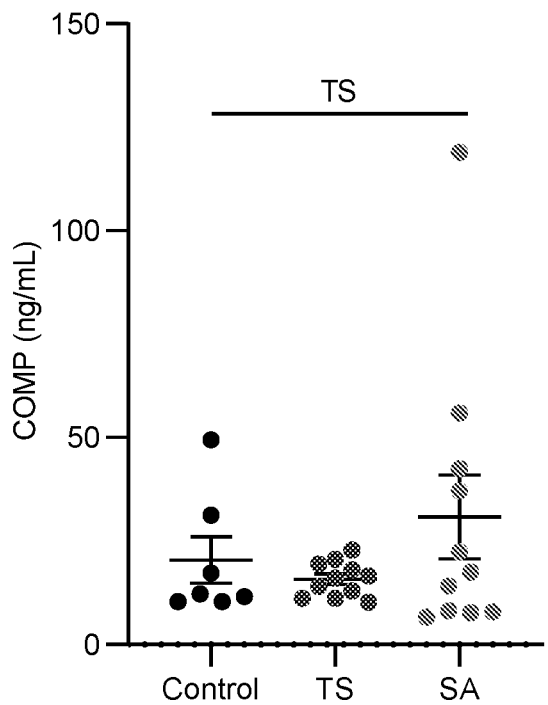
Figure 2F:
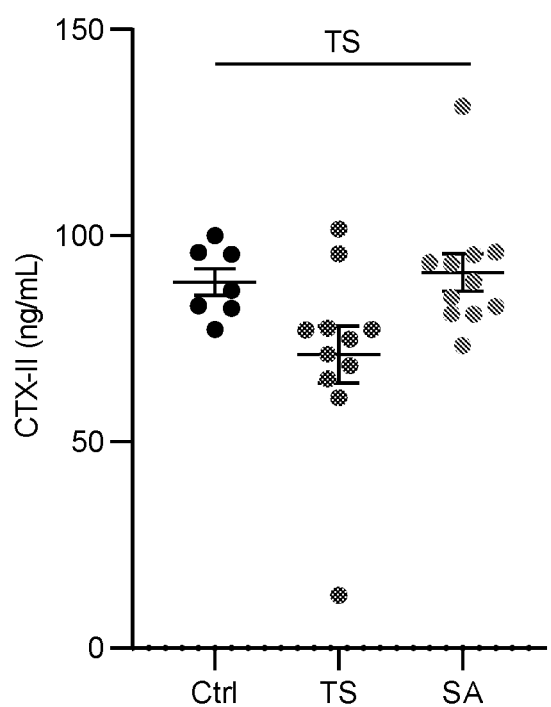

Septic arthritis, also known as infectious arthritis, represents a direct invasion of joint space by various microorganisms, most commonly caused by bacteria. Bacteria are the most significant pathogens in septic arthritis because of their rapidly destructive nature. Failure to recognize and to appropriately treat septic arthritis results in significant rates of morbidity and may even lead to death. The major consequence of bacterial invasion is damage to articular cartilage. This may be due to the particular organism's pathologic properties, such as the chondrocyte proteases of *S aureus*, as well as to the host's polymorphonuclear leukocytes response. The cells stimulate synthesis of cytokines and other inflammatory products, resulting in the hydrolysis of essential collagen and proteoglycans. Infection with *N gonorrhoeae* induces a relatively mild influx of white blood cells (WBCs) into the joint, explaining, in part, the minimal joint destruction observed with infection with this organism relative to destruction associated with *S aureus* infection.

Viral-mediated transient synovitis is inflammation of the synovial membrane. This membrane lines joints that possess cavities, known as synovial joints. The condition is usually painful, particularly when the joint is moved. The joint usually swells due to synovial fluid collection. Transient synovitis may occur in subjects when a viral infection, such as an upper respiratory infection, moves to and settles in the joint.

Osteomyelitis is inflammation of the bone caused by an infecting organism. Although bone is normally resistant to bacterial colonization, events such as trauma, surgery, the presence of foreign bodies, or the placement of prostheses may disrupt bony integrity and lead to the onset of bone infection. Osteomyelitis can also result from hematogenous spread after bacteremia. When prosthetic joints are associated with infection, microorganisms typically grow in biofilm, which protects bacteria from antimicrobial treatment and the host immune response.

Early and specific treatment is important in osteomyelitis, and identification of the causative microorganisms is essential for antibiotic therapy. The major cause of bone infections is *Staphylococcus aureus*. Infections with an open fracture or associated with joint prostheses and trauma often must be treated with a combination of antimicrobial agents and surgery. When biofilm microorganisms are involved, as in joint prostheses, a combination of rifampin with other antibiotics might be necessary for treatment.

The lack of new, disease-specific, serum diagnostic tests for musculoskeletal infections (septic arthritis versus osteomyelitis) versus non-bacterial etiologies, has hampered the ability to establish early diagnosis, permit rapid and accurate disease-specific treatments with a minimum of painful, invasive interventions, lower societal healthcare costs, and to minimize morbidity and maximize long-term outcomes. Since there have been no new laboratory tests clinical researchers have focused on optimization of currently available data points, the clinical history and laboratory tests, with the creation of prediction algorithms. Unfortunately published research on these prediction algorithms have produced conflicting results, and have not had a meaningful impact on patient care. Kocher et al. published a four criteria prediction algorithm in 1999 and identified WBC>/=12,000/cubic mm, febrile>/=38.5 degrees C., inability to bear weight, and ESR>/=40 (Kocher M S et al., J Bone Joint Surg [Am] 1999; 81:1662-70). If all four criteria were present, in their cohort, the likelihood of septic arthritis was 99.6%. However, in 2004, Luhmann et al. published on the use of these four criteria in our cohort in St. Louis, but could not replicate the findings of Kocher (Luhmann S J et al., J Bone Joint Surg [Am] 2004; 86:956-62). If all 4 criteria were present in the patients the likelihood of septic arthritis was only 59%, and the best prediction algorithm achieved was only a 71% chance of identifying septic arthritis (WBC>/=12,000/cubic mm, febrile>/=38.5° C., and previous evaluation by a healthcare provider). These algorithms can only indicate the risk the patient has septic arthritis, due to their non-specific nature.

To better understand the pathophysiology of musculoskeletal infections (e.g., septic arthritis and osteomyelitis) and non-bacterial etiologies such as transient synovitis, a standardized approach was applied to a number of subjects examining a panel of proteins using discriminant analysis to identify a set of biomarkers which accurately predicted whether a patient was diagnosed with septic arthritis, osteomyelitis or transient synovitis.

Based on the protein expression analysis disclosed herein, signatures correlating to disease occurrence and/or severity and signatures correlating to responsiveness/non-responsiveness to treatment have been identified and reported herein. Such biomarker signatures can be relied on to determine suitable treatment or adjust current therapy for subjects who need the treatment. Specifically, the biomarkers signatures are able to differentiate bacterial musculoskeletal infections from non-bacterial etiologies. In addition, discriminating between bacterial etiologies, septic arthritis and osteomyelitis, at the first evaluation obviates the need for painful diagnostic arthrocenteses, bone biopsies, expensive imaging tests, and inpatient admissions while increasing the precision of surgical and medical therapies.

Additional aspects of the disclosure are described below.
(I) Methods

One aspect of the present disclosure relates to methods for identifying a subject having or at risk for septic arthritis, or for determining disease severity of a septic arthritis subject (e.g., whether the subject has active disease), based on the septic arthritis protein signature as disclosed herein. In another aspect, of the present disclosure relates to methods for identifying a subject having or at risk for viral-mediated transient synovitis, or for determining disease severity of a transient synovitis subject (e.g., whether the subject has active disease), based on the transient synovitis protein signature as disclosed herein. In still another aspect of the present disclosure relates to methods for identifying a subject having or at risk for osteomyelitis, or for determining disease severity of an osteomyelitis subject (e.g., whether the subject has active disease), based on the osteomyelitis protein signature as disclosed herein.

(a) Protein Signatures

A protein signature refers to a characteristic expression profile of a single or a group of proteins that is indicative of an altered or unaltered biological process, medical condition, or a patient's responsiveness/non-responsiveness to a specific therapy. The septic arthritis or transient synovitis protein signature disclosed herein encompass characteristic expression profiles of at least one protein selected from TGFα, IL-7, IL-33 and IL-28A which are identified as differentially expressed in a biological sample obtained from a subject relative to a reference value. The osteomyelitis protein signature disclosed herein encompass characteristic expression profiles of at least one protein selected from procalcitonin, PIIANP, CTX-11 and C1-C2 which are identified as differentially expressed in a biological sample obtained from a subject relative to a reference value. See Examples below. In various embodiments, testing protein levels can be supplemented with diagnostic assays such as assays to determine presence, absence, and/or quantity of a pathogen, clinical assays (e.g., those described in the below examples), advanced radiographic assays, serum diagnostic assays, and aspiration.

In some embodiments, the present disclosure provides methods of diagnosis of a pathogen-associated disease in a subject. Additionally disclosed are methods of distinguishing the infectious etiology of a bacterial-caused infection (e.g., methicillin-resistant *S. aureus*, methicillin-sensitive *S. aureus* and non-staphylococcal infections).

The protein signatures as disclosed herein may represent the expression profile of at least one protein, for example, at least 2 proteins, at least 3 proteins, 4, proteins, 5 proteins, 6 proteins, 7 proteins, 8 proteins, 9 proteins, 10 proteins, 15 proteins, 20 proteins, 25 proteins, or more. In some examples, the protein signature may comprise multiple up-regulated proteins. In other examples, the protein signature may comprise multiple down-regulated proteins. In yet other examples, the protein signature may comprise both up-regulated and down-regulated proteins.

In some embodiments, the protein signature may comprise multiple proteins involved in multiple biological pathways, for example, 2 biological pathways, 3 biological pathways, 4 biological pathways, 5 biological pathways, 6 biological pathways, 7 biological pathways, 8 biological pathways, 9 biological pathways, 10 biological pathways, 11 biological pathways, 12 biological pathways, 13 biological pathways, 14 biological pathways, or 15 biological pathways.

In some examples, the septic arthritis or transient synovitis protein signature protein signature comprises at least one protein that is involved in cytokine activity. Non-limiting examples of proteins involved in cytokine activity to be used as biomarkers in the methods described herein include TGFα (e.g., GenBank Accession Nos. NP_001093161.1 and NM_001099691.2), IL-7 (e.g., GenBank Accession Nos. NP_000871.1 and NM_000880.3), IL-33 (e.g., GenBank Accession Nos. NP_001186569.1 and NM_001199640.1), IL-28A (e.g., GenBank Accession Nos. NP_742150.1 and NM_172138.1). In specific examples, the protein(s) involved in cytokine activity are TGFα, IL-7, IL-33, IL-28A or a combination thereof.

In some examples, the osteomyelitis protein signature comprises at least one protein that is involved in hormone signaling. In some examples, the osteomyelitis protein signature comprises at least one protein that is involved in extracellular matrix or a degradation product thereof. Non-limiting examples of proteins involved in hormone signaling to be used as biomarkers in the methods described herein include procalcitonin: peptide precursor of the hormone calcitonin. Non-limiting examples of proteins involved in extracellular matrix or a degradation product thereof include CTX-II: Type II collagen degradation, Type IIA Collagen N-Propeptide (PIIANP): type II collagen synthesis, and C1-2C Bone and Cartilage Degradation (C1-2C): type I and II collagen degradation.

In some embodiments, each of the above referenced protein signatures may include additional proteins or other factors, including in non-limiting examples erythrocyte sedimentation rate (ESR), C-reactive protein (CRP), white blood cell counts (WBC), alpha-defensin, IL-1 beta, IL-6, TNF-alpha, presepsin, MMP-9, lactate, CBC, IL-6, granulocyte-macrophage colony-stimulating factor, interferon-gamma, IL-1Beta, IL-2, IL-8, CD64, TIMP-1, calprotectin (CALP), Cartilage Oligomeric Matrix Protein (COMP), CS-846 Aggrecan Cartilage Synthesis (CS-846), Hyaluronan, Protectin, and/or IL-10.

(b) Determination of Protein Signatures

To determining any of the protein signatures as disclosed herein, the expression levels of the proteins involved in the septic arthritis, transient synovitis or osteomyelitis protein signature in a biological sample of a candidate subject can be measured by routine practice. In some examples, the protein expression levels can be mRNA levels of the target proteins. Alternatively, the protein expression levels can be represented by the levels of the protein products (encoded proteins). Assays for measuring levels of mRNA or proteins are known in the art and described herein. See, e.g., Molecular Cloning: A Laboratory Manual, J. Sambrook, et al., eds., Third Edition, Cold Spring Harbor Laboratory Press, Cold Spring Harbor, New York, 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York.

A subject to be assessed by any of the methods described herein can be a mammal, e.g., a human subject having septic arthritis, transient synovitis or osteomyelitis. A subject having septic arthritis, transient synovitis or osteomyelitis may be diagnosed based on clinically available tests and/or an assessment of the pattern of symptoms in a subject and response to therapy. In some embodiments, the subject is a pediatric subject. A pediatric subject may be of 18 years old or below. In some examples, a pediatric patient may have an age range of 0-12 years, e.g., 6 months to 8 years old or 1-6 years. In some instances, the subject may be free of a prior treatment for septic arthritis, transient synovitis or osteomyelitis, for example, free of any antibiotic or anti-viral treatment. In some instances, the subject may have received a prior treatment for septic arthritis, transient synovitis or osteomyelitis.

As used herein, the term "biological sample" refers to a sample obtained from a subject. A suitable biological sample can be obtained from a subject as described herein via routine practice. Non-limiting examples of biological samples include fluid samples such as blood (e.g., whole blood, plasma, or serum), urine, synovial fluid, and saliva, and solid samples such as tissue (e.g., skin, lung, or nasal) and feces. Such samples may be collected using any method known in the art or described herein, e.g., buccal swab, nasal swab, venipuncture, biopsy, urine collection, or stool collection. In some embodiments, the biological sample can be a blood sample. In one specific example, the biological sample is a serum sample.

In some embodiments, a single sample is obtained from a subject to detect the protein signature in the sample. Alternatively, the protein signature may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

In some embodiments, once a sample is obtained, it is processed in vitro to detect and measure the amount of the protein signature. All suitable methods for detecting and measuring an amount of a protein or protein product thereof known to one of skill in the art are contemplated within the scope of the invention. For example, epitope binding agent assays (i.e. antibody assays), enzymatic assays, electrophoresis, chromatography and/or mass spectrometry may be used. Non-limiting examples of epitope binding agent assays include an ELISA, a lateral flow assay, a sandwich immunoassay, a radioimmunoassay, an immunoblot or Western blot, flow cytometry, immunohistochemistry, and an array. The expression level(s) of the proteins involved in any of the protein signature as disclosed herein may be represented by the level of the mRNAs. Methods for detecting and/or assessing a level of nucleic acid expression in a sample are well known in the art, and all suitable methods for detecting and/or assessing an amount of nucleic acid expression known to one of skill in the art are contemplated within the scope of the invention. Non-limiting examples of suitable methods to assess an amount of nucleic acid expression may include arrays, such as microarrays, PCR, such as RT-PCR (including quantitative RT-PCR), nuclease protection assays and Northern blot analyses.

The level of expression of the target proteins may be normalized to the level of a control nucleic acid. This allows comparisons between assays that are performed on different occasions. For example, the raw data of protein expression levels can be normalized against the expression level of an internal control RNA (e.g., a ribosomal RNA or U6 RNA). The normalized expression level(s) of the proteins can then be compared to the expression level(s) of the same proteins of a control tissue sample, which can be normalized against the same internal control RNA, to determine whether the subject is likely to be responsive to a therapeutic treatment or non-responsive to a therapeutic treatment.

In another embodiment, the levels of the proteins can be determined by measuring the protein products at the protein level in a biological sample. In a specific embodiment, protein expression may be measured using an ELISA to determine the expression level of the proteins involved in the septic arthritis, transient synovitis or osteomyelitis protein signature as disclosed herein in a biological sample as also disclosed herein. Methods for detecting and/or assessing an amount of protein expression are well known in the art, and all suitable methods for detecting and/or assessing an amount of protein expression known to one of skill in the art are contemplated within the scope of the invention. Non-limiting examples of suitable methods to detect and/or assess an amount of protein expression may include epitope binding agent-based methods and mass spectrometry based methods.

Based on the expression levels of the involved proteins disclosed herein, a protein signature can be obtained via, e.g., a computational program. Various computational programs can be applied in the methods of this disclosure to aid in analysis of the expression data for producing the protein signature. Examples include, but are not limited to, Prediction Analysis of Microarray (PAM; see Tibshirani et al., PNAS 99(10):6567-6572, 2002); Plausible Neural Network (PNN; see, e.g., U.S. Pat. No. 7,287,014), PNNSulotion software and others provided by PNN Technologies Inc., Woodbridge, VA, USA, and Significance Analysis of Microarray (SAM). In some examples, a protein signature may be represented by a score that characterizes the expression pattern of the proteins involved in the protein signature.

(c) Assessing Disease Occurrence and/or Severity and Therapeutic Responsiveness Based on Protein Signature and Optionally Other Factors In an aspect, the disclosure provides a method to identify a subject having septic arthritis based on the expression profiles of at least one protein selected from TGFα, IL-7, IL-33 and IL-28A measured in a biological sample obtained from the subject. The method generally comprises (i) measuring the expression level of at least one protein selected from TGFα, IL-7, IL-33 and IL-28A, in the biological sample, (ii) determining if the protein expression is increased or decreased relative to a reference value, and (iii) identifying the subject as having or not having septic arthritis. In some embodiments, the subject is classified as having septic arthritis if the expression level of one or more of TGFα, IL-7, IL-33 and IL-28A are increased relative to the reference value. In some embodiments, the subject is classified as not having septic arthritis if the expression levels are the same or decreased relative to the reference value.

In another aspect, the disclosure provides a method to identify a subject having transient synovitis based on the expression profiles of at least one protein selected from TGFα, IL-7, IL-33 and IL-28A measured in a biological sample obtained from the subject. The method generally comprises (i) measuring the expression level of at least one protein selected from TGFα, IL-7, IL-33 and IL-28A, in the biological sample, (ii) determining if the protein expression is increased or decreased relative to a reference value, and (iii) identifying the subject as having or not having transient synovitis. In some embodiments, the subject is classified as having transient synovitis if the expression level of one or more of TGFα, IL-7, IL-33 and IL-28A are increased relative to the reference value. In some embodiments, the subject is classified as not having transient synovitis if the expression levels are the same or decreased relative to the reference value.

In still another aspect, the disclosure provides a method to identify a subject having osteomyelitis or differentiating a subject having osteomyelitis from a subject having septic arthritis based on the expression profiles of at least one marker selected from procalcitonin, Type II collagen degradation (CTX-II), Type IIA Collagen N-Propeptide (PIIANP), and C1-2C Bone and Cartilage Degradation (C1-2C) measured in a biological sample obtained from the subject. The method generally comprises (i) measuring the expression level of at least one marker selected from procalcitonin, PIIANP, CTX-11 and C1-C2, in the biological sample, (ii) determining if the protein expression is increased or decreased relative to a reference value, and (iii) identifying the subject as having or not having osteomyelitis. In some embodiments, the subject is classified as having osteomyelitis if the expression level of one or more of procalcitonin, PIIANP, CTX-11 and C1-C2 are increased relative to the reference value. In some embodiments, the subject is classified as not having osteomyelitis if the expression levels are the same or decreased relative to the reference value.

In still yet another aspect, the disclosure provides a method for monitoring septic arthritis, transient synovitis or osteomyelitis in a subject. In such an embodiment, a method of detecting the level of expression of the septic arthritis protein signature, transient synovitis protein signature or osteomyelitis protein signature, respectively, may be used to assess disease severity of a subject at one point in time. Then at a later time, the method of detecting the level of expression of the septic arthritis protein signature, transient synovitis protein signature or osteomyelitis protein signature may be used to determine the change in disease severity of the subject over time. For example, the method of detecting the level of expression of the septic arthritis protein signature, transient synovitis protein signature or osteomyelitis protein signature, may be used on the same subject days, weeks, months or years following the initial determination of the level of expression of the septic arthritis protein signature, transient synovitis protein signature or osteomyelitis protein signature. Accordingly, the method of detecting the level of expression of the septic arthritis protein signature, transient synovitis protein signature or osteomyelitis protein signature may be used to follow a subject over time to determine the rate of disease progression. For example, if the level of expression of the septic arthritis protein signature, transient synovitis protein signature or osteomyelitis protein signature is decreased relative to the level of expression of the septic arthritis protein signature, transient synovitis protein signature or osteomyelitis protein signature obtained from the same subject at an earlier time point, may indicate an abatement of disease progression. Alternatively, if the level of expression of the septic arthritis protein signature, transient synovitis protein signature or osteomyelitis protein signature is increased relative to the level of expression of the septic arthritis protein signature, transient synovitis protein signature or osteomyelitis protein signature obtained from the same subject at an earlier time point, may indicate disease progression.

Any of the protein signatures of a candidate subject as disclosed herein can be used for assessing whether the subject's responsiveness or non-responsiveness to a therapy, for example, an antibiotic or antiviral therapy. For example, the septic arthritis, transient synovitis or osteomyelitis protein signature of a candidate subject can be compared with a reference value. As used herein, assessing "responsiveness" or "non-responsiveness" to a therapeutic agent refers to the determination of the likelihood of a subject for responding or not responding to the therapeutic agent.

A reference value may represent the same protein signature of a control subject or represent the same protein signature of a control population. In some examples, the same protein signature of a control subject or a control population may be determined by the same method as used for determining the protein signature of the candidate subject. In some instances, the control subject or control population may refer to a healthy subject or healthy subject population of the same species (e.g., a human subject or human subject population having no disease). Alternatively, the control subject or control population may be a septic arthritis, transient synovitis or osteomyelitis patient or septic arthritis, transient synovitis or osteomyelitis patient population who is responsive to any of the therapeutic agents disclosed herein. In other instances, the control subject or control population may be a septic arthritis, transient synovitis or osteomyelitis patient or septic arthritis, transient synovitis or osteomyelitis patient population who is non-responsive to the therapeutic agent.

It is to be understood that the methods provided herein do not require that a reference value be measured every time a candidate subject is tested. Rather, in some embodiments, it is contemplated that the reference value can be obtained and recorded and that any test level can be compared to such a reference level. The reference level may be a single-cutoff value or a range of values.

By comparing the protein signature of a candidate subject as disclosed herein and a reference value as also described herein, the subject can be identified as responsive or likely to be responsive or as not responsive or not likely to be responsive to treatment based on the assessing.

For example, when the reference value represents the same protein signature of subjects who are responsive to a therapy, derivation from such a refer value would indicate non-responsiveness to the therapy. Alternatively, when the reference value represents the same protein signature of patients who are non-responsive to a therapy, derivation from such a reference value would indicate responsiveness to the therapy. In some instances, derivation means that the protein signature (e.g., represented by a score) of a candidate subject is elevated or reduced as relative to a reference value, for example, by at least 5%, 10%, 20%, 30%, 40%, 50%, 60%, 70%, 80%, 90%, 100%, 150%, 200%, 300%, 400%, 500% or more above or below the reference value.

It is to be understood that the methods provided herein do not require that a reference value be measured every time a candidate subject is tested. Rather, in some embodiments, it is contemplated that the reference value can be obtained and recorded and that any test level can be compared to such a reference level. The reference level may be a single-cutoff value or a range of values.

By comparing the UC occurrence and/or disease severity protein signature of a candidate subject as disclosed herein and a reference value as also described herein, the subject can be identified as having or at risk for the disease, or having active disease.

For example, when the reference value represents the same protein signature of healthy controls, derivation from such a reference value would indicate disease occurrence of risk for the disease. Alternatively, when the reference value represents the same protein signature of patients in inactive disease state, derivation from such a reference value would indicate active disease.

(c) Therapeutic Application of Protein Signatures

When a subject is determined to be responsive or non-responsive based on any of the protein signatures disclosed herein, this subject could be subjected to a suitable treatment for septic arthritis, transient synovitis or osteomyelitis, respectively, including any of the septic arthritis, transient synovitis or osteomyelitis treatments known in the art and disclosed herein. Alternatively, when a subject is determined as having or at risk for septic arthritis, transient synovitis or osteomyelitis or having active disease based on any of protein signatures as also disclosed herein, such a subject may be given a suitable anti-septic arthritis, anti-transient synovitis or anti-osteomyelitis therapy, for example, those described herein. Thus, as described herein, a subject having a septic arthritis, transient synovitis or osteomyelitis can be treated by any method known in the art suitable for treating the disease. Therapeutic agents and methods of treating a septic arthritis, transient synovitis or osteomyelitis are well known in the art.

For example, a therapeutic agent can be any agent suitable for treating a septic arthritis, transient synovitis or osteomyelitis or any agent suitable to avoid septic arthritis, transient synovitis or osteomyelitis.

As another example, a therapeutic agent can be an antibiotic such as methicillin, glycopeptide, tetracycline, oxytetracycline, doxycycline; chlortetracycline, minocycline, glycylcycline, cephalosporin, ciprofloxacin, nitrofurantoin, trimethoprim-sulfa, piperacillin/tazobactam, moxifloxacin, vancomycin, teicoplanin, penicillin, and macrolide. As another example a therapeutic agent can be an antiviral agent (e.g., a broad-spectrum antiviral or viral specific antiviral), such as oseltamivir (Tamiflu), zanamivir (Relenza), and peramivir (Rapivab). As another example, a therapeutic agent can be an anti-inflammatory agent. Non-limiting examples of anti-inflammatory agents include sulfasalazine, mesalamine, balsalazide, olsalazine, or corticosteroids (e.g., prednisone or budesonide). In some embodiments, treatment comprises surgery.

Non-limiting examples of surgery include debridement, drainage of the infected site, arthrocenteses, and bone biopsies.

The term "treating" as used herein refers to the application or administration of a composition including one or more active agents to a subject, who has septic arthritis, transient synovitis or osteomyelitis, a symptom of septic arthritis, transient synovitis or osteomyelitis, or a predisposition toward septic arthritis, transient synovitis or osteomyelitis, with the purpose to cure, heal, alleviate, relieve, alter, remedy, ameliorate, improve, or affect the disease, the symptoms of the disease, or the predisposition toward the disease. An "effective amount" is that amount of an anti-septic arthritis, anti-transient synovitis or anti-osteomyelitis agent that alone, or together with further doses, produces the desired response, e.g. eliminate or alleviate symptoms, prevent or reduce the risk of flare-ups (maintain long-term remission), and/or restore quality of life. The desired response is to inhibit the progression of the disease. This may involve only slowing the progression of the disease temporarily, although more preferably, it involves halting the progression of the disease permanently. This can be monitored by routine methods or can be monitored according to diagnostic and prognostic methods discussed herein.

The desired response to treatment of the disease or condition also can be delaying the onset or even preventing the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Any of the methods described herein can further comprise adjusting the septic arthritis, transient synovitis or osteomyelitis treatment performed to the subject based on the results obtained from the methods disclosed herein (e.g., based on protein signatures disclosed herein). Adjusting treatment includes, but are not limited to, changing the dose and/or administration of the anti-septic arthritis, anti-transient synovitis or anti-osteomyelitis agent used in the current treatment, switching the current medication to a different anti-septic arthritis, anti-transient synovitis or anti-osteomyelitis agent, or applying a new septic arthritis, transient synovitis or osteomyelitis therapy to the subject, which can be either in combination with the current therapy or replacing the current therapy.

In some embodiments, the present disclosure provides a method for treating a subject (e.g., a human patient) having septic arthritis, transient synovitis or osteomyelitis, the method comprising administering an effective amount of an anti-septic arthritis, anti-transient synovitis or anti-osteomyelitis agent (e.g., those disclosed herein) to a subject who exhibits a protein signature indicative of having septic arthritis, transient synovitis or osteomyelitis.

Generally, a safe and effective amount of a therapeutic agent is, for example, that amount that would cause the desired therapeutic effect in a subject while minimizing undesired side effects. In various embodiments, an effective amount of a therapeutic agent described herein can substantially inhibit infection, slow the progress of infection or limit the development of infection.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a therapeutic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to inhibit heart failure, coronary heart disease, or cardiac related death, slow the progress of heart failure or coronary heart disease or limit the development of heart failure or coronary heart disease.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are proteinrally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a therapeutic agent can occur as a single event or over a time course of treatment. For example, a therapeutic agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a cardiovascular disease, disorder, or condition.

A therapeutic agent can be administered simultaneously or sequentially with another agent, such as an antibiotic, an anti-inflammatory, or another agent. For example, a therapeutic agent can be administered simultaneously with another agent, such as an antibiotic or an anti-inflammatory. Simultaneous administration can occur through administration of separate compositions, each containing one or more of a therapeutic agent, an antibiotic, an anti-inflammatory, or another agent. Simultaneous administration can occur through administration of one composition containing two or more of a therapeutic agent, an antibiotic, an anti-inflammatory, or another agent. A therapeutic agent can be administered sequentially with an antibiotic, an anti-inflammatory, or another agent. For example, a therapeutic agent can be administered before or after administration of an antibiotic, an anti-inflammatory, or another agent.

II. Kits

Also provided are kits. Such kits within the scope of this disclosure are kits for use in assessing the protein signatures disclosed herein in a subject, such as a human subject. Such a kit can comprise reagents for determining the level(s) of proteins involved in any of the protein signature (see section I). The reagents can be oligonucleotide probes/primers for determining the mRNA levels of the target proteins. Alternatively, the kit can contain antibodies specific to one or more of these protein products. In specific examples, the kit comprises reagents for determining the levels of one or more of TGFα, IL-7, IL-33, IL-28A, procalcitonin, Type II collagen degradation (CTX-II), Type IIA Collagen N-Propeptide (PIIANP), and C1-2C Bone and Cartilage Degradation (C1-2C). Such kits can facilitate performance of the methods described herein. When supplied as a kit, the different components of the composition can be packaged in separate containers and admixed immediately before use. Components include, but are not limited to a biological sample of a subject, ceramide containing calibration standards, a blank, a blank with internal standards, QC samples (LQC, MQC, and HQC), or BSA solutions. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In order to better understand the pathophysiology of musculoskeletal infections, researchers have recently begun to investigate into the areas of host immune response and cartilage and bone physiology (specifically production and degradation). Joint-based research using synovial fluid for biomarker and cytokine analysis have identified alpha-defensin, IL-1 beta, IL-6, TNF-alpha, presepsin, MMP-9, lactate, and alpha-defensin as possible markers for septic arthritis (Deirmengian C et al., Clin Orthop Relat Res 2010; 468:2017-23; Deirmengian C et al., Clin Orthop Relat Res 2015; 473:2229-35; Ettinger M et al., Clin Infect Dis 2015;

61:332-41; Fotopoulos V C et al., Knee Surg Sports Traumatol Arthrosc 2012; 20:1159-67; Imagama T et al., A preliminary study. J Infect Chemother 2019; 25:170-4; Lenski M et al., Acta Orthop Belg 2014; 80:18-25; Logters T et al., J Orthop Res 2009; 27:1401-7; et al., Osiri M et al., Asian Pac J Allergy Immunol 1998; 16:155-60; Pupaibool J et al., Int Orthop 2016; 40:2447-52; Shu E et al., Am J Emerg Med 2019; 37:502-5). Frangiamore et al. reported the analysis of synovial fluid of 75 pts undergoing revision total shoulder arthroplasty (TSA) and identified elevated levels of IL-6, granulocytemacrophage colony-stimulating factor, interferon-gamma, IL-1 Beta, IL-2, IL-8 and IL-10 in infected TSA (Frangiamore et al., J Shoulder Elbow Surg 2017; 26:186-96). The best test to identify infected TSAs was a panel of synovial IL-6, TNF-alpha, and IL-1, which demonstrated sensitivity of 0.80, specificity of 0.93, PPV 0.87 and NPV 0.89, +LR 12.0, −LR 0.21. Analysis of synovial fluid should demonstrate elevation of multiple biomarker and cytokine levels in septic arthritis, mainly due to the joint space and synovial fluid being the epicenter for the infectious process. The drawback to the use of synovial fluid diagnostically is the acquisition of synovial fluid which is painful, may require intravenous sedation and additional imaging studies (i.e. ultrasound or fluoroscopy), and requires healthcare centers with higher level of resources and physician training.

The use of serum for detection of septic arthritis has many clinical advantages over the use of synovial fluid, specifically the ease of acquisition and lower costs, since obtaining an adequate sample is accomplished by routine venipuncture, and greater accessibility to healthcare providers. Two serum assays, procalcitonin and leucocyte esterase, have been studied in the diagnostic work-up of septic arthritis and osteomyelitis. Unfortunately, the studies on both have reported conflicting findings on their diagnostic utility.

Over the last 6 years other serum biomarkers, TNF-alpha, CD64, TIMP-1, CTX-II and calprotectin have been reported to be potential discriminators between septic arthritis and non-septic arthritis etiologies. Talebi-Taher et al, demonstrated TNF-alpha was significantly elevated in septic arthritis versus controls (Talebi-Taher M et al. Rheumatol Int 2013; 33:319-24). Oppegaard et al, reported CD64 had high specificity (98%) but poor sensitivity (<60%) in differentiating septic arthritis from inflammatory or crystal-induced arthritis (Oppegaard 0 et al., BMC Infect Dis 2013; 13:278). The most interesting study to date was published in 2019 by Couderc et al (Couderc M et al., Joint Bone Spine 2019; 86:261-2). This study analyzed the use of nine serum and synovial biomarkers to differentiate septic arthritis from non-septic arthritis etiologies (i.e. chondrocalcinosis, gout, rheumatoid arthritis, spondyloarthritis) in 42 adult patients. Synovial MMP-9, C-terminal telopeptide of type II collagen (CD(−11), calprotectin (CALP) and serum TIMP-1, CD(−11, and calprotectin were elevated in septic arthritis patients (p<0.05). When serum TIMP-1 and synovial CTX-II were combined and thresholds of 286.5 ng/ml and 873 ng/ml were used, respectively, the sensitivity was 75% and the specificity was 94% for diagnosing SA. This combination correctly patients in 86% of cases. Interestingly, TNF alpha and CTX-II levels were not statistically different between septic arthritis and transient synovitis patients in the present examples.

Thus, the presentation of the non-traumatic acutely painful joint/limb poses a diagnostic dilemma due to the similarity of presentations of the most likely diagnoses (septic arthritis, transient synovitis, osteomyelitis). Current diagnostic tools employed to differentiate these diagnoses are cumbersome and rely on non-specific inflammatory markers (WBC/ESR/C-RP), radiography (XR, CT, ultrasound), and often arthrocentesis, an invasive and expensive procedure. In an effort to streamline the diagnostic process and reduce patient morbidity, the present disclosure provides a broad, multiplex array of protein signatures (e.g., cytokines and tissue degradation products) on serum of pediatric patients presenting with a chief compliant of atraumatic joint/limb pain. The present Example identifies a 4-cytokine serum panel that differentiates septic arthritis (SA) from transient synovitis (TS) in the pediatric population with superior sensitivity and specificity than previously proposed serum based diagnostic markers. In addition, the present examples provide the identification of septic arthritis, transient synovitis and osteomyelitis protein signatures. In turn, the results provide the ability to correctly detect disease etiology and thus guide treatment decisions.

Methods 22 age-matched patients presenting with joint/extremity pain whose working diagnosis included septic arthritis or transient synovitis were enrolled. Serum samples were collected from each patient at time presentation. Each sample underwent a seven-ELISA panel (C1-C2, COMP, CS-846, hyaluronan, procalcitonin, PIIANP, CTX-II) and a 65-plex Cytokine Panel. Definitive diagnosis was based on laboratory tests, arthrocentesis results, and clinical scenario.

Patients presenting with a chief complaint of an irritable hip or knee at a single tertiary care children's hospital were prospectively enrolled. A peripheral blood sample was obtained from each enrolled patient as part of their routine diagnostic evaluation. Serum was isolated from each blood sample and stored for analysis of various serum proteins at a later date. The study was approved by an institutional review board and all patients were enrolled with proper informed consent and documentation. Patient demographics and routine laboratory values are listed in Table 1 below.

TABLE 1

| Variable | Septic Arthritis (N = 11) * | Transient Synovitis (N = 11) * | P-value |
|---|---|---|---|
| Age (mos) | 67.1 ± 35.4 | 60.5 ± 32.6 | 0.63 |
| Male gender (%) | 83.3 | 53.8 | 0.2 |
| Symptom Duration (days) | 1.6 ± 1.0 | 2.6 ± 1.4 | 0.07 |
| Joint (%) | | | |
| Hip | 50 | 76.9 | 0.23 |
| Knee | 33.3 | 23.1 | 0.67 |
| Ankle | 8.3 | 0 | 1 |
| Shoulder | 8.3 | 0 | 1 |
| Fever >38.0 (%) | 41.7 | 23.1 | 0.41 |
| Imaging (%) | | | |
| XR | 100 | 100 | 1 |
| Ultrasound | 58.3 | 61.5 | 1 |
| CT | 8.3 | 0 | 1 |
| MRI | 41.7 | 23.1 | 0.41 |
| WBC (K/ccm) | 10.9 ± 1.9 | 11.0 ± 3.6 | 0.96 |
| ESR (mm/H) | 56.6 ± 29.6 | 12.4 ± 12.4 | 0.0002 |
| CRP (mg/L) | 59.2 ± 81.1 | 15.7 ± 24.1 | 0.08 |
| Aspiration | | | |
| Frequency (%) | 91.7 | 30.8 | 0.004 |
| Nucleated cell count | 76411.1 ± 68498.7 | 4759.3 ± 3000.7 | 0.12 |
| PMN frequency | 87.4 ± 8.2 | 71.7 ± 15.5 | 0.04 |

*The values for continuous variables are given as the mean and standard deviation A total of 25 patients with a chief complaint of hip, knee, shoulder, or ankle pain were enrolled. All evaluations included a history, physical exam, laboratory studies, with a complete blood cell count with differential, measure of the erythrocyte sedimentation rate and C-reactive protein. Additional serum analyses such as blood cultures were performed on the basis of the physician's preference and the clinical presentation. Plain radiographs of the indicated joint were made for all patients. Additional imaging modalities including ultrasound, CT scan, and MRI were performed at the discretion of the treating physician. If a hip effusion was documented, arthrocentesis was performed under fluoroscopic guidance in the radiology or operating suite, with arthrographic confirmation of intra-articular position of the needle. Analysis of the synovial fluid included a white blood-cell count and differential, Gram stain, and culture.

Medical records were reviewed for patient age, gender, disease history (duration of symptoms, fever, weight bearing status), clinical findings, radiographic assessment and findings, results of arthrocentesis, laboratory studies, and treatment. Fever was defined as an oral temperature >38.4° C. The diagnosis of septic arthritis (12 patients) was assigned based on a combination of clinical features (refusal to bear weight, pain with range of motion of involved joint), elevated inflammatory markers (ESR or C-RP), positive blood and/or synovial cultures, and a synovial white blood-cell count >50,000 cells/mm3. All patients with the diagnosis of septic arthritis were confirmed by one of the following criteria: gross purulence in the synovial space visualized intra-operatively, positive bacterial culture growth from synovial fluid aspiration or fluid or tissue culture obtained intra-operatively. The diagnosis of transient synovitis was assigned based on a combination of negative blood and/or synovial cultures, normal ESR and C-RP values, synovial white blood-cell count <50,000 cells/mm3, or resolution of symptoms without intravenous antibiotics or surgical intervention. After evaluation, patients with the diagnosis of transient synovitis were treated with oral analgesics, typically non-steroidal anti-inflammatory agents. Patients with the diagnosis of septic arthritis (based on clinical appearance and aspiration results and confirmed intra-operatively) underwent emergent surgical drainage of the involved joint and were started on empiric intravenous antibiotics.

Sixty-five serum cytokines and chemokines were quantified in 29 human serum samples (11 septic arthritis, 11 transient synovitis, and 7 control) using a Human Cytokine/Chemokine 65-Plex Panel Routine Discovery Assay using a Millipore MILLIPLEX Assay Kit (Eve Technologies, Alberta, CA). Additionally, patient and control serum was analyzed for the presence and abundance of the following cartilage biosynthetic molecules according to the manufacturer's instructions: Collagen type I and II cleavage products (C1,2C, IBEX Pharmaceuticals Inc.), Human Cartilage Oligometric Matrix Protein (COMP, BioVendor Research and Diagnostic Products), Aggrecan Chondroitin Sulfate 846 Epitope (CS-846, IBEX Pharmaceuticals), Procalcitonin (Thermo Scientific), Hyaluronan (R&D Systems), Type IIA procollagen N-propeptide (PIIANP, EMD Millipore), C-terminal telopeptide of type II collagen (CTx-II, LifeSpan BioSciences, Inc.).

Univariate analyses were performed with the use of the two-sample Student t test for continuous variables and the Fisher exact test for categorical variables. Linear discriminant analysis was used to identify a linear combination of biomarkers from that predicted a diagnosis of septic arthritis or transient synovitis. All of the predictors were continuous numeric variables. The selection of predictors was performed via stepwise discriminant analysis using SAS v. 9.4 with an entry and retention criteria of P=0.05. The selected group of predictors from the stepwise discriminant analysis was used to generate the final linear combination of these predictors and summary output. The accuracy of the classification was assessed using sensitivity and specificity, calculated from the cross-tabulation of concordant and discordant diagnosis predictions by the linear combination model (classification summary). Both re-substitution and cross-validation were used to generate the cross-tabulation.

Results (i) Protein Signatures for Diagnosing Septic Arthritis or Transient Synovitis.

A unique set of cytokines or ELISA predictors accurately predicted whether a patient was diagnosed with septic arthritis or transient synovitis. Using TGF-a, IL-7, IL-33, and IL-28A, 20 out of the 22 cases were accurately classified, having a sensitivity and specificity of 90.9% (95% confidence interval: 73.9%, 100.0%). See FIGS. 4-5.

(ii) Protein Signatures for Diagnosing Osteomyelitis.

In a second set analysis of biomarkers and cytokines (procalcitonin, PIIANP, CTX-II and C1-C2) were able to correctly differentiate septic arthritis from osteomyelitis in 20 of the 22 cases.

(iii) Distinguishing Transient Synovitis from Septic Arthritis Requires a Combinatorial Clinical Evaluation, Radiographic Assessment, and Serum/Joint Aspiration Analysis.

Over a three-year period, 25 patients who presented in the acute care setting (Emergency Department, Orthopaedic Surgery clinic) with a chief complaint of a painful joint or extremity and were able to provide informed consent for participation in the study were enrolled. On the basis of clinical, radiographic, and laboratory studies the working diagnosis for these patients included septic arthritis (SA) and transient synovitis (TS). Additionally, serum was collected in the pre-operative period from 7 healthy control patients that presented for routine removal of hardware surgeries. These control serum samples were used in biochemical assays to compare serum protein levels in transient synovitis and septic arthritis patients relative to appropriate population norms. Serum was collected from these patients at the time of initial evaluation in the office of emergency department. Based on clinical, radiographic, serum, and culture parameters, patients were diagnosed with either SA (n=12) or transient synovitis (n=13). Diagnosis of SA was confirmed by visualization of purulence in the affected joint intra-operatively or positive bacterial culture from aspiration or intra-operative tissue culture collection of the painful joint. Diagnosis of TS was indirectly confirmed by resolution with conservative measures including NSAIDs. 11 of 12 SA patients and 11/13 TS patients had serum available for further cytokine/chemokine/cartilage biosynthesis product analysis, while 11 of 13 TS patients had serum available. A flowchart of patient enrolment, diagnosis, and analysis is diagrammed in FIG. 1. Patients diagnosed with septic arthritis underwent operative incision and drainage of the affected joint and were treated with intravenous antibiotics for an average of 3-5 days followed by a 4-6 week course of oral antibiotic therapy.

At the time of presentation: 1) body temperature >/=38.5° F. was present in 42% of SA (5/12), and 23% (3/13) TS patients (p=0.41), 2) mean ESR in the SA group was 56.6 mm/hr and 12.4 mm/hr in the TS group (p<0.001), 3) mean CRP was 59.3 mg/dl in the SA group and 15.7 mg/dl in the TS group (p=0.08), and 4) mean WBC was 10.9 K/mm3 in the SA group and 11.0 K/mm3 in the TS group (p=0.96). Plain radiographs of the involved joint were obtained in 100% of patients in the TS and SA groups. 7/12 (58.3%) of SA patients and 8/13 (61.5%) were evaluated for the presence of an effusion in the involved joint by ultrasound. Furthermore advanced imaging (MRI, CT) was obtained prior to diagnosis in 23% of TS patients with TS and 50% of SA patients. On the basis of clinical, radiographic, and serum laboratory evidence, aspiration of the involved joint was obtained in 92% of patients diagnosed with SA (11/12) and 31% of patients diagnosed with TS (4/13). The mean aspiration cell count in the SA group was and in the TS group (p=0.12). The mean aspiration PMN frequency was 87.4% in the SA group and 71.7% in TS group (p=0.04).

Overall the differentiation of TS from SA was reliable and feasible in a clinically timely manner. However reaching these diagnoses accurately was aided by a combination of clinical, advanced radiographic, serum, and aspiration results. As such, patients ultimately diagnosed with the benign condition of TS were frequently subjected to costly and invasive tests including ultrasound, MRI, and joint aspiration.

(iv) Serum Levels of Cartilage Biosynthesis/Cleavage Products do not Reliably Differentiate Septic Arthritis from Transient Synovitis.

Virulent bacterial infections contained within the synovial space, and the subsequent robust inflammatory response against these infectious agents can result in rapid degradation of synovial cartilage, thus necessitating rapid diagnosis and treatment of septic arthritis. Transient synovitis similarly is an immune mediated condition but lacks the presences of a localized virulent factor and thus does not pose the same threat of cartilage degradation. Thus it was suggested that the presence of cartilage degradation products or precursors in cartilage synthesis (indicative of cartilage turnover) in serum could distinguish septic arthritis from transient synovitis and control patients. The concentration of C1-2C bone and cartilage degradation product (C1-C2), cartilage oligometric matrix protein (COMP), CS-846 aggrecan cartilage synthesis (CS-846), hyaluronan, type IIA collage n-propeptide (PIIANP), and C-terminal telopeptide of type II collagen (CTX-II) were evaluated in the serum of previously identified control, viral synovitis, and septic arthritis patients using ELISA based assays. Interestingly, and contrary to the suggestion, no significant differences in levels of cartilage degradation/synthesis products in the serum of patients with SA, TS, or control patients (FIG. 2A-2E). Thus, serum evaluation of cartilage degradation and biosynthesis products is not reliable for the diagnosis of septic arthritis or viral synovitis.

(v) Procalcitonin does not Differentiate Septic Arthritis from Viral Synovitis

Figure 3:
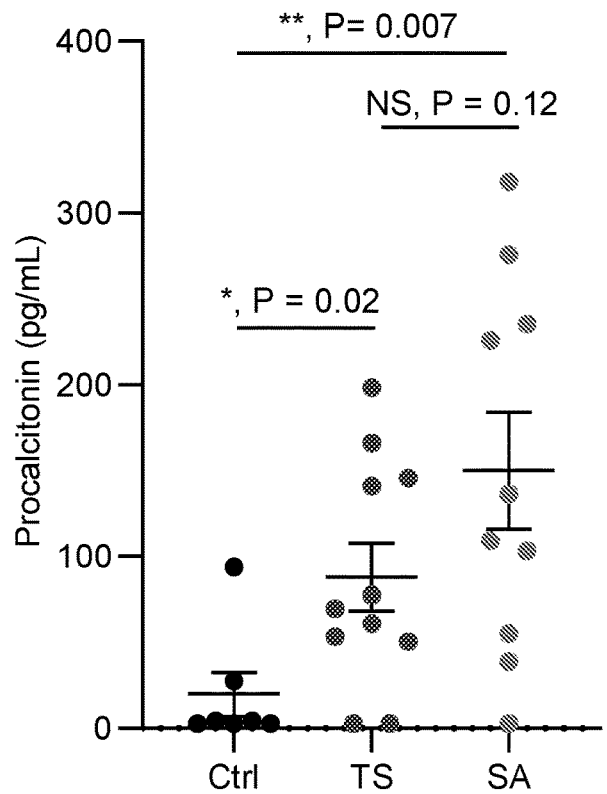
FIG. 3 shows procalcitonin performed poorly in differentiating septic arthritis from viral synovitis.
Figure 4A:
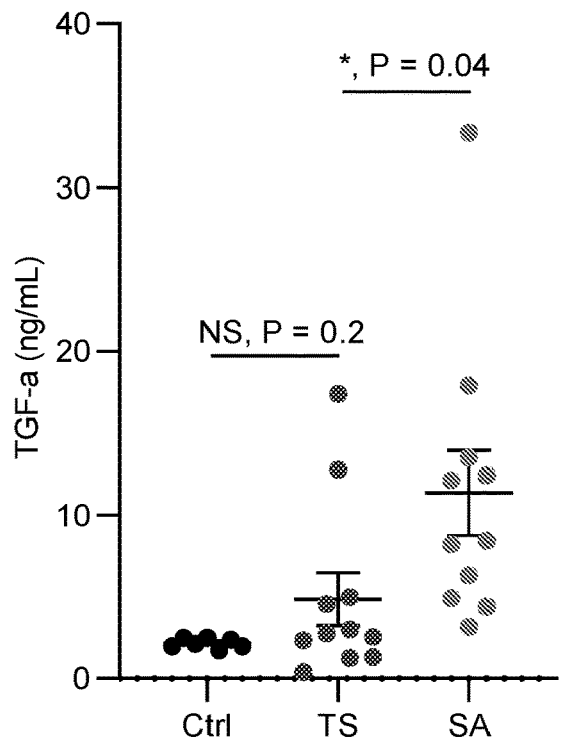
FIG. 4A-4D are graphs showing the serum concentration of Transforming growth factor alpha (TGF-α), interleukin 7 (IL-7), interleukin 33 (IL-33), and interleukin 28 (IL-28A).
Figure 4B:
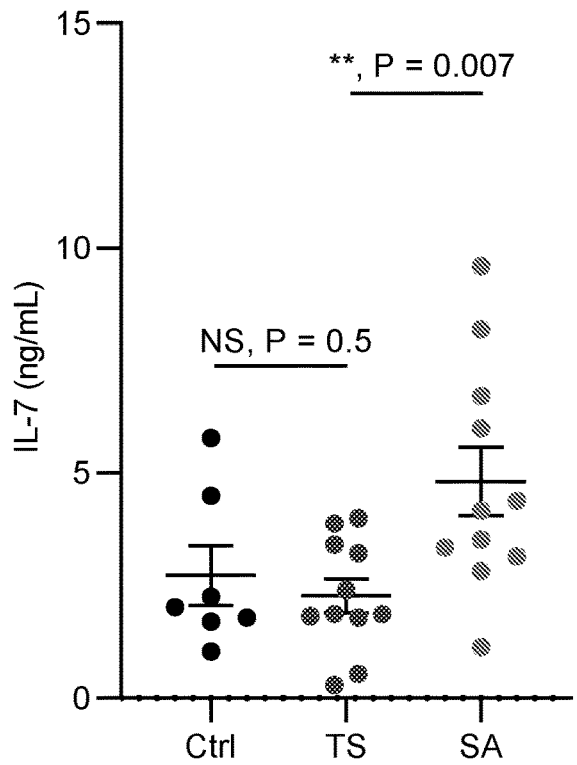
Figure 4C:
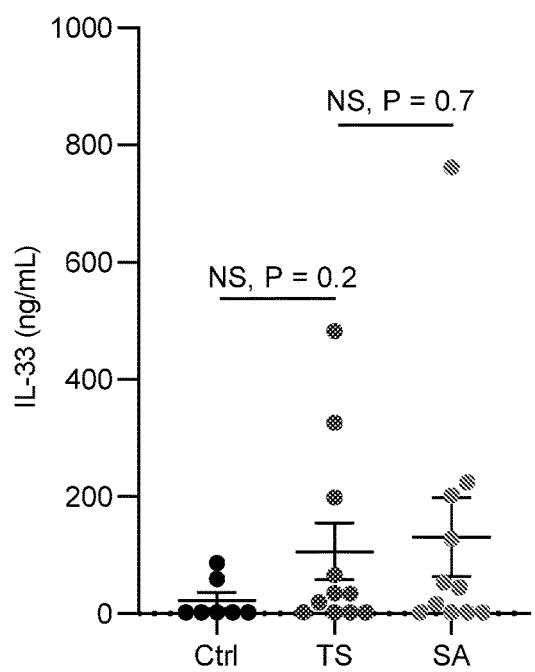
Figure 4D:
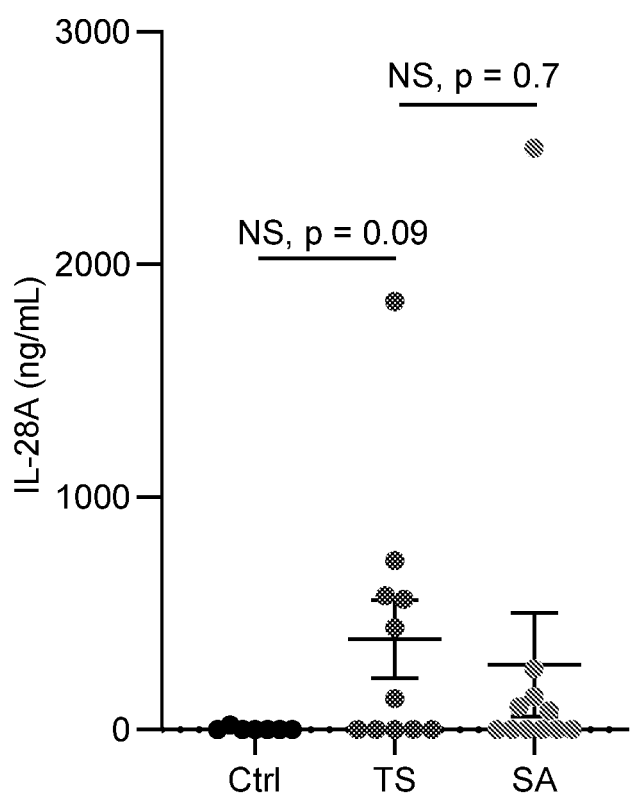

Procalcitonin is a 116 amino acid protein that is secreted into the bloodstream during severe bacterial infection. While the thyroid gland is the conventional source of procalcitonin, other cell types including leukocytes have been shown to secrete procalcitonin under pro-inflammatory conditions. Procalcitonin has demonstrated moderate efficacy in differentiating septic arthritis from transient synovitis in retrospective studies. Thus procalcitonin was evaluated as a diagnostic tool in differentiating septic arthritis from viral synovitis in our patient cohort. Concurrent with previous studies, it was found that procalcitonin is elevated in septic arthritis patients compared to non-infected controls. However, procalcitonin performed poorly in differentiating septic arthritis from viral synovitis (FIG. 3). Thus, in the cohort of patients evaluated in the current study, and consistent with recently published results, serum procalcitonin was a poor diagnostic tool in differentiating septic arthritis from viral synovitis.

(vi) A Serum-Based 4-Cytokine Panel Distinguishes SA from Control and Viral Synovitis Patients In response to diverse infectious and non-infectious stimuli, distinct cellular components of the human immune system produce a myriad of soluble molecules known as cytokines and chemokines. These molecules regulate a variety of processes including immune cell recruitment, activation, and pathogen elimination. In response to distinct activating stimuli the immune system generates a diversity of responses characterized by distinct cytokine/chemokine profiles. Given the distinct pathogenesis of septic arthritis and transient synovitis, it was suggested that systemic cytokine/chemokine profiles would be distinct between these pathologies. Thus a 65 unique panel or cytokines and chemokines were measured in the serum of patients with viral synovitis, septic arthritis, and healthy controls (FIG. 5). Using linear discriminant analysis, a combination of biomarkers capable of predicting septic arthritis from transient synovitis was identified. The discriminant analysis identified a reduced set of 4 cytokines: Transforming growth factor alpha (TGF-α), interleukin 7 (IL-7), interleukin 33 (IL-33), and interleukin 28 (IL-28A) (FIG. 4). Specifically, TGF-α, a growth factor produced macrophages, and IL-7, a hematopoietic growth factor, were significantly increased in SA relative to TS or control patients. IL-33 and IL-28A were not able to distinguish SA from TS patients in isolation but are important modifiers in the logistical regression analysis. Using this 4-cytokine panel in the total cohort of TS and SA patients, 20 out of 22 cases were accurately classified having a sensitivity and specificity of 90.9% (95% confidence interval: 73.9%-100%) (Table 2, below). By comparison, using the conventional cut-off of 40 mm/H, serum ESR was able to correctly identify 10/11 TS patients (90.9%), but 6/11 SA patients were correctly diagnosed by ESR alone (54.5%). Using the conventional cut-off of 20 mg/L, serum CRP was correctly able to identify 6/11 SA patients (54.5%) and 8/11 TS patients (72.7%). Thus, it was unexpectedly discovered that utilizing a non-supervised, multiplex cytokine assay, a 4-cytokine panel capable of distinguishing septic arthritis from transient synovitis with greater sensitivity and specificity than previously described serum biomarkers without the need for invasive joint aspiration. This was unexpected as the identified panel was able to more accurately distinguish SA and TS than when using the gold standard assays.

TABLE 2

Number of Observations and Percent Classified

| From Group | Into Group | | |
|---|---|---|---|
| | Septic Arthritis | Synovitis | Total |
| Septic Arthritis | 10 | 1 | 11 |
| | 90.91 | 9.09 | 100.00 |
| Synovitis | 1 | 10 | 11 |
| | 9.09 | 90.91 | 100.00 |
| Total | 11 | 11 | 22 |
| | 50.00 | 50.00 | 100.00 |

(vii) Characterization of Septic Arthritis, Transient Synovitis, or Osteomyelitis Subjects.

Serum is collected from 60-80 patients, after the patient enrollment process, during the routine lab draws completed during the diagnostic work up. Demographic, radiographic, laboratory test values, microbiological culture results, medical and surgical treatment are collected for each patient. A second sample of serum is collected 48 hours after admission for all enrolled patients who are admitted to the hospital, which include all septic arthritis and osteomyelitis and synovitis patients. The second sample creates the opportunity to assess the cytokines and biomarkers' levels after a 48 hour interval to quantify tissue damage (e.g. C1-2C and COMP) and to determine if levels correlate with the clinical course of the patient (e.g. symptom resolution) and traditional laboratory tests (ESR, CRP and CBC). Blood samples are be coded, collected, processed and stored. After completion of a patient's musculoskeletal care episode, each sample is labeled with a final diagnosis based on the clinical presentation, laboratory data (blood cultures, arthrocentesis cultures), operative findings, and the clinical course of the patient.

Control patients are recruited from patients from the Orthopaedic Surgery service (<18 years of age), who are ASA 1 or 2, and undergoing elective implant removal for healed fractures without any existing cofounding variables (i.e. history of surgical site infection, inflammatory disease). Blood is drawn after the patient was induced under general anesthesia, during intravenous catheter placement, and prior to the surgical implant removal.

A 10-biomarker assay and 65-cytokine panel is run on all samples and analyzed based on final diagnosis:
1. C1-2C Bone and Cartilage Degradation (C1-2C): type I and II collagen degradation
2. Cartilage Oligomeric Matrix Protein (COMP): cartilage degradation
3. CS-846 Aggrecan Cartilage Synthesis (CS-846): cartilage aggrecan synthesis/turnover
4. Hyaluronan: synovitis, synovial tissue degradation
5. Procalcitonin: peptide precursor of the hormone calcitonin; can differentiate between systemic infection (sepsis) and localized infection
6. Type IIA Collagen N-Propeptide (PIIANP): type II collagen synthesis
7. CTX-II: Type II collagen degradation
8. TIMP-1: natural inhibitor of the matrix metalloproteinases (MMPs), a group of peptidases involved in degradation of the extracellular matrix
9. CD64: monocyte and macrophage receptor; triggers phagocytosis and cytokine release in early immune response
10. Protectin: role as an anti-inflammatory and anti-apoptotic molecule which may halt viral proliferation To assure the accuracy each assay kit has reference wells to confirm assay accuracy and reliability.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Discussion

The differential diagnosis for a pediatric patient with atraumatic joint/limb pain is extensive, but the most common diagnoses included transient synovitis and septic arthritis. Due to similarities in clinical presentation, distinguishing between these two pathologies is often invasive, expensive, and time consuming. Current diagnostic algorithms rely on various imaging modalities, non-specific serum markers of inflammation, and synovial fluid analysis. Moreover, timely and accurate diagnosis is of paramount importance as therapies for these two pathologies are non-overlapping—anti-inflammatory agents for viral synovitis and surgical debridement and antibiotics for septic arthritis. Inaccurate classification of transient synovitis as to unnecessary advanced imaging, invasive aspiration tests, and even in rare instances, non-indicated surgery. Conversely, delayed treatment of true septic arthritis can lead to irreversible cartilage degradation and premature joint destruction. As such, there remains a need for minimally invasive, efficient diagnostic tools for deciphering septic arthritis from transient synovitis without compromising accuracy.

Transient synovitis and septic arthritis cause joint pain/irritation by distinct mechanisms. Septic arthritis is an infection of the synovial space often introduced via hematogenous inoculation. The etiology of transient synovitis is controversial, but unlike septic arthritis, it is not caused by direct infection of the synovial space. Another inappropriate inflammatory reaction that affects the synovium, often in the post-viral period, has been proposed as a predominant etiology of transient synovitis. Both pathologies involve an inflammatory reaction, but given the distinct pathogenic mechanisms, we hypothesized that the systemic inflammatory cascade would be distinct and distinguishable in septic arthritis and transient synovitis. In this study we utilized a non-biased assessment of multiple serum cytokines and chemokines as a surrogate of the systemic immune response. Through these investigations, a 4-cytokine panel was identified that is capable of distinguishing septic arthritis from viral synovitis with >90% sensitivity and specificity, superior to traditional serum based diagnostic assays such as ESR, CRP, and procalcitonin in the current patient cohort.

Thus a novel serum based cytokine panel was discovered to identify septic arthritis, potentially negating the need for more invasive tests such as arthrocentesis as well as costly and time-inefficient imaging modalities such as MRI. This cytokine-based diagnostic tool focuses on the distinct pathologic processes between septic arthritis and transient synovitis and as such performs superior to more conventional, non-specific inflammatory markers in distinguishing these pathologies.

The efficient diagnosis and treatment of septic arthritis is critical to avoid cartilage destruction and permanent joint damage and dysfunction. Transient synovitis, while causing patient discomfort and distress, does not pose the same long-term risk to joint health. Thus it was suggested that markers of cartilage breakdown and biosynthesis could be utilized to differentiate between septic arthritis and transient synovitis. Interestingly, no differences in these products in patients with septic arthritis compared to viral synovitis or healthy control patients were detected. Similarly, despite recent reports suggesting procalcitonin's utility as a diagnostic tool distinguishing SA from viral synovitis, the tested patient cohort, procalcitonin performed poorly in distinguishing these pathologies. Thus it was concluded that procalcitonin, similar to ESR and CRP, is better considered a non-specific marker of inflammation than it is a distinguishing factor between TS and SA.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of identifying and treating a subject having septic arthritis, the method comprising:
   i) measuring expression levels of proteins comprising TGFα, IL-7, IL-33 and IL-28A in a blood sample obtained from the subject;
   ii) determining a septic arthritis protein signature based on the expression levels of the proteins in step (i); and
   iii) assessing septic arthritis occurrence or severity of the subject based on the protein signature determined in step (ii); and
   iv) administering a therapeutically effective amount of a therapeutic agent to the subject based on the septic arthritis occurrence or severity determined in step (iii), wherein the therapeutic agent is selected from the group consisting of an antibiotic, an antiviral agent, and an anti-inflammatory agent.

2. The method of claim 1, wherein the blood sample is a serum sample.

3. The method of claim 1, wherein the expression levels of the proteins are measured by an epitope binding agent assay, enzymatic assay, electrophoresis, chromatography, mass spectrometry, RT-PCR or microarray analysis.

4. The method of claim 1, wherein the subject is identified as having or at risk for septic arthritis and the method further comprises subjecting the subject to a treatment of septic arthritis.

5. The method of claim 1, wherein the subject has undergone a prior treatment for septic arthritis.

6. The method of claim 1, wherein increased expression levels of the protein measured in step (i) relative to a reference value indicates the subject has septic arthritis.

7. The method of claim 6, wherein increased TGFα or IL-7 relative to a reference value of a subject having transient synovitis indicates the subject has septic arthritis.

* * * * *